US012767915B2

(12) United States Patent
Ling

(10) Patent No.: US 12,767,915 B2
(45) **Date of Patent: *Oct. 20, 2026**

(54) THREE-DIMENSIONAL BIOREACTOR FOR VIRAL VECTOR PRODUCTION

(71) Applicant: SOUTHWEST RESEARCH INSTITUTE, San Antonio, TX (US)

(72) Inventor: Jian Ling, Spring Branch, TX (US)

(73) Assignee: SOUTHWEST RESEARCH INSTITUTE, San Antonio, TX (US)

( * ) Notice: Subject to any disclaimer, the term of this patent is extended or adjusted under 35 U.S.C. 154(b) by 986 days.

This patent is subject to a terminal disclaimer.

(21) Appl. No.: 17/301,625

(22) Filed: Apr. 9, 2021

(65) Prior Publication Data

US 2021/0317396 A1 Oct. 14, 2021

Related U.S. Application Data

(60) Provisional application No. 63/008,441, filed on Apr. 10, 2020.

(51) Int. Cl.
*C12M 1/00* (2006.01)
*C12M 1/12* (2006.01)

(52) U.S. Cl.
CPC ............ *C12M 25/14* (2013.01); *C12M 23/02* (2013.01); *C12M 29/10* (2013.01)

(58) Field of Classification Search
CPC ...... C12M 25/14; C12M 23/02; C12M 29/10; C12M 23/20
See application file for complete search history.

(56) References Cited

U.S. PATENT DOCUMENTS

| | | | | |
|---|---|---|---|---|
| 5,443,950 | A | 8/1995 | Naughton et al. | |
| 7,678,572 | B2 | 3/2010 | Har-Noy | |
| 7,956,164 | B2 | 6/2011 | Har-Noy | |
| 8,007,823 | B2 | 8/2011 | Favis | |
| 8,012,750 | B2 | 9/2011 | Har-Noy | |
| 8,463,418 | B2 | 6/2013 | Liu et al. | |
| 8,961,892 | B2 * | 2/2015 | Hutter | B01F 35/92 502/527.24 |
| 9,410,114 | B2 | 8/2016 | Wilson et al. | |
| 9,456,893 | B2 | 10/2016 | Ling | |
| 9,512,393 | B2 | 12/2016 | Kasuto et al. | |

(Continued)

FOREIGN PATENT DOCUMENTS

| | | | |
|---|---|---|---|
| CN | 108866013 A * | 11/2018 | C12M 23/14 |
| EP | 3351656 | 7/2018 | |

(Continued)

OTHER PUBLICATIONS

Office Action from related Korean Appln. No. 10-2020-7031766, dated Jul. 11, 2022. English translation attached.

(Continued)

*Primary Examiner* — Liban M Hassan
(74) *Attorney, Agent, or Firm* — Secant IP, PLLC

(57) ABSTRACT

The present disclosure relates to the design, fabrication, and applications of a three-dimensional (3D) bioreactor for expansion of viral vector producing cells and ultimate harvesting of viral vectors. The bioreactor is composed of non-random interconnected voids providing a continuous three-dimensional surface area for cell adherence and growth.

18 Claims, 24 Drawing Sheets

(56) References Cited

U.S. PATENT DOCUMENTS

| | | | | |
|---|---|---|---|---|
| 9,593,308 | B2 | 3/2017 | Har-Noy | |
| 9,663,763 | B2 | 5/2017 | Sentman | |
| 10,052,372 | B2 | 8/2018 | Wang et al. | |
| 10,131,876 | B2 | 11/2018 | Kaiser et al. | |
| 10,179,151 | B2 | 1/2019 | Ferber | |
| 10,450,574 | B2 | 10/2019 | Johnson et al. | |
| 10,577,585 | B2 | 3/2020 | Nguyen et al. | |
| 2003/0119185 | A1 | 6/2003 | Berenson et al. | |
| 2004/0062809 | A1 | 4/2004 | Honiger et al. | |
| 2006/0121005 | A1 | 6/2006 | Berenson et al. | |
| 2008/0194010 | A1 | 8/2008 | Liu | |
| 2008/0248572 | A1 | 10/2008 | Antwiler | |
| 2010/0273667 | A1 | 10/2010 | Kotev et al. | |
| 2012/0009159 | A1 | 1/2012 | Humayun et al. | |
| 2013/0084622 | A1 | 4/2013 | Ram et al. | |
| 2015/0087057 | A1 | 3/2015 | Zink et al. | |
| 2015/0140333 | A1 | 5/2015 | Niu | |
| 2016/0200891 | A1 | 7/2016 | Virgilio et al. | |
| 2017/0028042 | A1 | 2/2017 | Wang et al. | |
| 2017/0051309 | A1 | 2/2017 | Lesch et al. | |
| 2017/0081638 | A1 | 3/2017 | Ma | |
| 2017/0312392 | A1 | 11/2017 | Guilak et al. | |
| 2017/0321178 | A1 | 11/2017 | Ling | |
| 2018/0016533 | A1 | 1/2018 | Tai et al. | |
| 2018/0057784 | A1 | 3/2018 | Wang et al. | |
| 2018/0142199 | A1* | 5/2018 | Jones | C12M 21/08 |
| 2018/0142200 | A1 | 5/2018 | Mason et al. | |
| 2019/0002815 | A1 | 1/2019 | Wang et al. | |
| 2019/0032011 | A1 | 1/2019 | Better et al. | |
| 2019/0169572 | A1 | 6/2019 | Shi et al. | |
| 2019/0211292 | A1 | 7/2019 | Beauchesne | |
| 2019/0269768 | A1 | 9/2019 | Wang et al. | |
| 2019/0276846 | A1 | 9/2019 | Lipponen et al. | |
| 2019/0292517 | A1 | 9/2019 | Cheung et al. | |
| 2019/0309250 | A1 | 10/2019 | Ling | |
| 2020/0071670 | A1 | 3/2020 | Shi et al. | |
| 2020/0157483 | A1 | 5/2020 | Ling et al. | |
| 2020/0172864 | A1 | 6/2020 | Chiang et al. | |
| 2020/0181562 | A1 | 6/2020 | Mcafee et al. | |
| 2020/0190457 | A1 | 6/2020 | Veraitch et al. | |
| 2020/0208121 | A1 | 7/2020 | Hewitt et al. | |
| 2020/0248121 | A1 | 8/2020 | Ferrie et al. | |
| 2020/0248122 | A1 | 8/2020 | Ferrie et al. | |
| 2020/0248123 | A1 | 8/2020 | Ferrie et al. | |
| 2020/0248124 | A1 | 8/2020 | Ferrie et al. | |
| 2020/0255783 | A1 | 8/2020 | Ferrie et al. | |
| 2020/0255790 | A1 | 8/2020 | Veraitch et al. | |
| 2020/0255793 | A1 | 8/2020 | OConnor et al. | |
| 2020/0283712 | A1 | 9/2020 | Wang et al. | |

FOREIGN PATENT DOCUMENTS

| | | | | |
|---|---|---|---|---|
| EP | 3447120 | | 2/2019 | |
| JP | 2005503156 | | 2/2005 | |
| JP | 2007-500015 | | 1/2007 | |
| JP | 2010517590 | | 5/2010 | |
| JP | 2010-523118 | | 7/2010 | |
| JP | 2019-500030 | | 1/2019 | |
| KR | 10-2013-0134080 | | 12/2013 | |
| WO | 94/03496 | | 2/1994 | |
| WO | 9850522 | | 11/1998 | |
| WO | 2004087797 | A1 | 10/2004 | |
| WO | 2008101001 | | 8/2008 | |
| WO | 2008140295 | | 11/2008 | |
| WO | 2011072393 | | 6/2011 | |
| WO | 2012168295 | | 12/2012 | |
| WO | 2014037862 | | 3/2014 | |
| WO | 2015001321 | | 1/2015 | |
| WO | 2015024133 | A1 | 2/2015 | |
| WO | 2015086029 | A1 | 6/2015 | |
| WO | 2017049066 | | 3/2017 | |
| WO | 2017099712 | | 6/2017 | |
| WO | WO-2017096039 | A1 * | 6/2017 | C12N 15/85 |
| WO | 2017/180724 | | 10/2017 | |
| WO | 2017192717 | A1 | 11/2017 | |
| WO | 2017204235 | | 11/2017 | |
| WO | 2018005521 | | 1/2018 | |
| WO | 2018013797 | | 1/2018 | |
| WO | WO-2018049420 | A1 * | 3/2018 | C12M 1/00 |
| WO | 2019/104069 | | 5/2019 | |
| WO | 2019194842 | A1 | 10/2019 | |
| WO | 2020068840 | A1 | 4/2020 | |

OTHER PUBLICATIONS

Choi, et al "Three-Dimensional Scaffolds for Tissue Engineering: The Importance of Uniformity in Pore Size and Structure" American Chemical Society, Langmuir Article published on Web Nov. 23, 2010, 26(24), pp. 19001-19006.

Lee, et al: "Three-Dimensional Cell Culture Matrices: State of the Art"; Tissue Engineering: Part B, vol. 14, No. 1, 2008, pp. 61-86.

Petrie Aronin, C., et al: "Comparative Effects of Scaffold Pore Size, Pore Volume and Total Void Volume on Cranial Bone Healing Patterns Using Microsphere-based Scaffolds" Journal of Biomedical Materials Research Part A, Wiley InterScience Periodicals, Inc. published online Apr. 28, 2008 pp. 632-641.

Zeltinger, Ph.D., J., et al: "Effect of Pore Size and Void Fraction on Cellular Adhesion, Proliferation, and Matrix Deposition"; Tissue Engineering, vol. 7, No. 5, 2001, Mary Ann Liebert, Inc.; downloaded by EPO from <<www.ieberpub.com>> on Nov. 22, 2019 (pp. 557-572).

Extended European Search Report issued in corresponding European Patent Appln No. 1779329.8; mail date Dec. 5, 2019 (16 pgs).

1st Written Opinion issued in corresponding Singapore AppIn No. 11201809805W; mail date Feb. 4, 2020 (6 pgs).

International Search Report; mailed Jan. 23, 2020; issued in related PCT/US2019/52719 (11 pgs).

Office Action from related Korean Appln. No. 10-2018-7035015, dated Aug. 30, 2021, (12 pgs).

Alves De Silva, et al., "Chondrogenic Differentiation of Human Bone Marrow Mesenchymal Stem Cells in Chitosan-Based Scaffolds Using a Flow-Perfusion Bioreactor", Journal of Tissue Engineering and Regenerative Medicine, J Tissue Eng Regen Med 5: 722-732, John Wiley & Sons, Ltd, published online Dec. 30, 2010.

Arifin, et al., "Ultraviolet/ozone Treated Polystyrene Microcarriers for Animal Cell Culture", J Chem Technol Biotechnol, pp. 2607-2619, published online Dec. 26, 2015.

Boland, et al., "In Vitro Cytotoxicity of a Low-Shrinkage Polymerizable Liquid Crystal Resin Monomer", Journal of Bioedical Materials Research Part B; Applied Biomaterials, pp. 4-6, published online Feb. 27, 2006.

Caicedo-Carvajal, "3D Perfusion Bioreactor: The Cumulative Advantages or 3D Scaffold Geometry and Perfusion for Scale-up Processes", 3D Biotek, Technology of New Jersey, (7 pgs).

Chen, et al., "Scaffold Design for Tissue Engineering", Macromolecular Bioscience, Wiley-VCH Verlag GmbH, 2002, 2, pp. 67-77.

Cheung, et al., "Scaffolds that mimic antigen-presenting cells enable ex vivo expansion of primary T cells", Nature Biotechnology, Springer Nature, vol. 36, No. 2, Feb. 2018, pp. 160-169.

Choi, et al., "Neovascularization in Biodegradable Inverse Opal Scaffolds with Uniform and Precisely Controlled Pore Sizes", Advanced Healthcare Materials, 2013, 2, Wiley-VCH Verlag GmbH & Co., pp. 145-154.

Choi, et al. "Alzheimer's Disease and Stem Cell Therapy", Experimental Neurobiology, pp. 45-52.

Dynabeads Human T-Activator CD3/CD28 for T Cell Expansion and Activation, https://www.thermofisher.com/order/catalog/product/11161D, Aug. 2018, (4 pages).

Elkasabi, et al., "Towards Multipotent Coatings: Chemical Vapor Deposition and Biofunctionalization of Carbonyl-Substituted Copolymers", Macromol. Rapid Commun. 2008, 29, Wiley-VCH Verlag GmbH & Co., pp. 855-870.

Fenge, et al., "Large-Scale Perfusion and Concentrated Fed-Batch Operation of Biostat® STR Single-Use Bioreactor", Sartorius Stedim Biotech, Publication No. SBT1018-e13061, Order No. 85037-541-22, Ver. 06, 2013, (6 pages).

(56) References Cited

OTHER PUBLICATIONS

Frith, et al., "Dynamic Three-Dimensional Culture Methods Enhance Mesenchymal Stem Cell Properties and Increase Therapeutic Potential", Tissue Engineering, Part C, vol. 16, No. 4, 2010, Mary Ann Liebert, Inc., pp. 735-750.
Gardel, et al., "A Novel Bidirectional Continuous Perfusion Bioreactor for the Culture of Large-Sized Bone Tissue-Engineered Constructs", J BiomedMater Res Part B 2013:101B:1377-1386.
Allied Market Research, "Gene Therapy Market—Global Opportunity Analysis and Industry Forecast, 2017-2023", https://www.reportlinker.com/p05371879/Gene-Therapy-Market-Global-Opportunity-Analysis, Apr. 5, 2020, (7 pages).
Allied Market Research, "Gene Therapy Market Size, Share & Industry Analysis 2026", https://www.alliedmarketresearch.com/gene-therapy-market, Apr. 5, 2020, (19 pages).
Geng, et al., "Ultrafast Multi-Focus 3-D Nano-Fabrication Based on Two-Photon Polymerization", Nature Communications, 2019, pp. 1-7.
GE Life Sciences, "WAVE Bioreactor Systems Cell Culture Procedures", GE Healthcare Bio-Sciences, Sweden, 2008, (52 pages).
Glavaski-Joksimovic, et al., "Mesenchymal Stem Cells and Neuroregeneration in Parkinson's Disease", Experimental Neurology, vol. 247, Elsevier, 2013, pp. 25-38.
Gordon, et al., "The Chemistry of Chlorine Dioxide", Progress in Inorganic Chemistry, vol. 15, John Wiley and Sons, Inc., 1972, pp. 201-286.
Ligon, et al., "Polymers for 3D Printing and Customized Additive Manufacturing", Chemical Reviews, ACS Publications vol. 117, 2017, pp. 10212-10290.
Han, et al., "High-Performance Nano-Photoinitiators with Improved Safety for 3D Printing", ACS Applied Materials & Interfaces, vol. 9, 2017, pp. 32418-32423.
Higuera, et al., "The Physics of Tissue Formation with Mesenchymal Stem Cells", Trends in Biotechnology, vol. 31, No. 11, Elsevier Ltd., 2012, pp. 583-590.
Kaiser, et al., "Towards a Commercial Process for the Manufature of Genetically Modified T Cells for Therapy", https://www.nature.com/articles/cgt201478, Mar. 26, 2018, pp. 1-25.
Kaepylae, et al., "Direct Laser Writing and Geometrical Analysis of Scaffolds with Designed Pore Architecture for Three-Dimensional Cell Culturing", Journal of Micromechanics and Microengineering, vol. 22, 2012, pp. 1-13.
Kim, et al., "Bioreactor Strategy in Bone Tissue Engineering: Pre-Culture and Osteogenic Differentiation Under Two Flow Configurations", Tissue Engineering: Part A, vol. 18, No's. 21 and 22, 2012, pp. 2354-2364.
Ko, et al., "One Step Immobilization of Peptides and Proteins by Using Modified Parylene with Formyl Groups", Biosensors and Bioelectronics, vol. 30, Elsevier, 2011, pp. 56-60.
Kumar, et al., "Human Mesenchymal Stem Cells Expansion on Three-Dimensional (3D) Printed Poly Styrene (PS) Scaffolds in a Perfusion Bioreactor", Procedia CIRP, vol. 65, Elsevier, 2017, pp. 115-120.
Kumar, et al., "Large Scale Industrialized Cell Expansion: Producing the Critical Raw Material for Biofabrication Processes", Biofabrication, vol. 7, IOP Publishing, 2015, pp. 1-15.
Kwon, et al., "Microfluidic Cell Retention Device for Perfusion of Mammalian Suspension Culture", Scientific Reports, vol. 7, No. 6703, Springer Nature, 2017, pp. 1-32.
Lechanteur, et al., "Large-Scale Clinical Expansion of Mesenchymal Stem Cells in the GMP-Compliant, Closed Automated Quantum® Cell Expansion System: Comparison with Expansion in Traditional T-Flasks", Journal of stem Cell Research & Therapy, vol. 4, Issue 8, 2014, pp. 1-11.
Manceur, et al., "Scalable Lentiviral Vector Production Using Stable HEK293SF Producer Cell Lines", Human Gene Therapy Methods, vol. 28, No. 6, Published by Mary Ann Liebert, Inc., 2017, pp. 330-339.
MAS.865 2018 How to Make Something that Makes (almost) Anything, http://fab.cba.mit.edu/classes/865.18/additive/multiphoton-polymerizatio . . . , Mar. 30, 2020, pp. 1-10.
Mirro, "An Update on the Advantages of Fibra-Cel® Disks for Cell Culture", Eppendorf Application Note, No. 313, 2011, (3 pages).
Papadimitropoulos, et al., "Expansion of Human Mesenchymal Stromal Cells from Fresh Bone Marrow in a 3D Scaffold-Based System under Direct Perfusion", Plos One, vol. 9, Issue 7, 2014, pp. 1-12.
Poertner, et al., "Fixed Bed Reactors for the Cultivation of Mammalian Cells: Design, Performance and Scale-Up", The Open Biotechnology Journal, vol. 1, Bentham Science Publishers, Ltd., 2007, pp. 41-46.
Provin, et al., "A Method for the Design of 3D Scaffolds for High-Density Cell Attachment and Determination of Optimum Perfusion Culture Conditions", Journal of Biomechanics, vol. 41, Elsevier, 2008, pp. 1436-1449.
Rout-Pitt, et al., "Large-Scale Production of Lentiviral Vectors Using Multilayer Cell Factories", Journal of Biological Methods, vol. 5(2), POL Scientific, 2018, pp. 1-9.
Sailon, et al., "A Novel Flow-Perfusion Bioreactor Supports 3D Dynamic Cell Culture", Journal of Biomedicine and Biotechnology, vol. 2009, Article ID 873816, Hindawi Publishing Corporation, 2009, pp. 1-8.
Schop, et al., "Expansion of Mesenchymal Stem Cells Using a Microcarrier-Based Cultivation System: Growth and Metabolism", Journal of Tissue Engineering and Regenative Medicine, vol. 2, John Wiley & Sons, Ltd. 2008, pp. 126-135.
Specialty Coating Systems., "SCS Parylene Properties", Indianapolis, IN, 2014, 12 pgs.
Sobral, et al., "Three-Dimensional Plotted Scaffolds with Controlled Pore Size Gradients; Effect of Scaffold Geometry on Mechanical Performance and Cell Seeding Efficiency", Acta Biomaterialia, vol. 7, Elsevier, 2011, pp. 1009-1018.
Tan, et al., "Surface Engineering and Patterning Using Parylene for Biological Applications", Materials Journal, vol. 3, MDPI, 2010, pp. 1803-1832.
Nanoscribe Gmbh, "Think Big, Print Nano. Your Partner for High-Precision Additive Manufacturing", https://www.nanoscribe.com/en/, Mar. 30, 2020, (7 pages).
Valkama, et al., "Optimization of Lentiviral Vector Production for Scale-Up in Fixed-Bed Bioreactor", Gene Therapy, vol. 25, Nature Portfolio, 2018, pp. 39-46.
Van Den Driesche, et al., 3D Printing Solutions for Microfluidic Chip-to-World Connections, Micromachines Journal, vol. 9, MDPI, 2018, Basel, Switzerland, (12 pages).
Vitale, et al., "Frontal Conversion and Uniformity in 3D Printing by Photopolymerisation", Materials vol. 9, MDPI, 2016, Basel, Switzerland, (13 pages).
Weber, et al., "Production process for stem cell based therapeutic implants: expansion of the production cell line and cultivation of encapsulated cells", Adv Biochem Eng Biotechnol, vol. 123, Springer Link, 2010, pp. 143-162.
Wellinghoff, et al., "Advanced Dental Restorative Composites Utilizing Low Polymerization Shrinkage Liquid Crystalline Monomers", (8 pages).
Wen, et al., "Repair Mechanisms of Bone Marrow Mesenchymal Stem Cells in Myocardial Infarction", Journal of Cellular and Molecular Medicine, vol. 15, No. 5, Blackwell Publishing, Ltd., 2011, pp. 1032-1043.
Whitford, et al., "Single-Use, Continuous Processing of Primary Stem Cells", BioProcess International, vol. 12(3)s, 2014, pp. 26-33.
Nanoscribe Gmbh, "A Wide Range of Aplications in Research, Prototyping and Production Processes", https://www.nanoscribe.com/en/applications, Mar. 30, 2020, (11 pages).
Wu, et al., "Mesenchymal Stem Cell-Based Therapy for Type 1 Diabetes", Discovery Medicine, vol. 17(93), 2014, pp. 139-143.
Yamada, et al., "Multi-Sized Sphere Packing", Japan, 2009, pp. 1-45.
Yang, "Mussel-Inspired Encapsulation and Functionalization of Individual Yeast Cells", Journal of the American Chemical Society, vol. 133, ACS Publications, 2011, pp. 2795-2797.

(56) References Cited

OTHER PUBLICATIONS

Yeatts, "Bioreactors to Influence Stem Cell Fate: Augmentation of Mesenchymal Stem Cell Signaling Pathways via Dynamic Culture Systems", Biochimica et Biophysica Acta 1830, Elsevier, 2013, pp. 2470-2480.
Yourek, "Shear Stress Induces Osteogenic Differentiation of Human Mesenchymal Stem Cells", Regenerative Medicine, 5(5), Future Science Group, 2010, pp. 713-724.
Zhang, "Fabrication of Three Dimensional Polymeric Scaffolds with Spherical Pores", Journal of Materials Science, vol. 41, Springer Science + Business Media, Inc., 2006, pp. 1725-1731.
International Search Report and the Written Opinion, mailed Jan. 23, 2020, in corresponding PCT Appln. No. PCT/US19/52713, 12 pgs.
International Search Report and the Written Opinion, mailed Jul. 23, 2021, in corresponding PCT Appln. No. PCT/US2021/070371, 9 pgs.
International Search Report and the Written Opinion, mailed Aug. 2, 2017, in corresponding PCT Appln. No. PCT/US17/30833, 14 pgs.
Office Action from related Japanese Appln. No. 2021-516622, dated Oct. 11, 2022. English translation attached.
Office Action from related Singaporean Appln. No. 11202102986X dated Oct. 21, 2022.
First Office Action from related Australian Appln. No. 2017261267, mailed Jan. 17, 2022, 6 pages.
Office Action from related Japanese Appln. No. 2020-554460, dated Apr. 11, 2022. English translation attached.
Written Opinion from corresponding Singapore Appln. No. 11202009803T, dated May 24, 2022.
Supplemental Partial European Search Report from related Application No. 19866434.4, mailed Jun. 9, 2022.
Office Action from related Indian Appln. No. 202017046644, dated Sep. 7, 2022. English translation attached.
Office Action from related Korean Appln. No. 10-2021-7011941, dated Oct. 26, 2023. English translation attached.
Office Action from related Australian Appln. No. 2021253701, dated Oct. 19, 2023.
Office Action from related Chinese Appln. No. 201880093563.6, dated Sep. 16, 2023. English translation attached.
Office Action from related Chinese Appln. No. 201980071515.1, dated Nov. 17, 2023. English translation attached.
Office Action from related Indian Appln. No. 201817044901, dated Feb. 16, 2021. English translation attached.
International Search Report and Written Opinion from related PCT Appln. No. PCT/US2018/031027, dated Jul. 23, 2018.
Neunstoecklin, "DASGIP Parallel Bioreactor Systems for cell culture applications", 2022, Germany, pp. 1-4.
Extended European Search Report from related EP Appln. No. 21785732.5, dated Mar. 17, 2025.
Office Action from related Japanese Appln. No. 2022-561146, dated Feb. 25, 2025. English translation attached.
Extended European Search Report from related EP Appln. No. 22873908.2, dated Jul. 15, 2025.
Chun et al., "Patchwise bone microstructure reconstruction", The 2021 World Congress on Advances in Structural Engineering and Mechanics, S. Korea, 2021, pp. 1-5.
Guha et al., Deep learning based high-resolution reconstruction of trabecular bone microstructures from low-resolution CT scans using GAN-CIRCLE, Proceedings of SPIE, vol. 11317, 2020, U.S., pp. 1-12.
Xie et al., "Super-Resolution reconstruction of Bone Micro-Structure Micro-CT Image based on Auto-Encoder Structure", Proceedings of the IEEE International Conference on Robotics and Biomimetics, China, 2019, pp. 1568-1575.

* cited by examiner

THREE-DIMENSIONAL BIOREACTOR FOR VIRAL VECTOR PRODUCTION

CROSS-REFERENCE TO RELATED APPLICATIONS

This application claims the benefit of U.S. Provisional Application Ser. No. 63/008,441 filed Apr. 10, 2020, which is fully incorporated herein by reference.

FIELD OF THE INVENTION

The present disclosure relates to the design, fabrication, and applications of a three-dimensional (3D) bioreactor for expansion of viral vector producing cells and ultimate harvesting of viral vectors. The bioreactor is composed of non-random voids interconnected through non-random pores providing a continuous three-dimensional surface area for cell adherence and growth. Such 3D bioreactor is also scalable with a defined geometry, surface coating, and fluidic dynamics to maintain a monolayer cell culture and reduce or prevent cell aggregation, phenotype change, or extracellular production, and is particularly suitable for culturing of HEK 293T cells providing lentiviral vectors under appropriate surface coating of the bioreactor. The invention can also extend to produce other types of viruses and vaccines based on live-attenuated viruses, or inactivated viruses, or viral vectors.

BACKGROUND

Gene modification to cells is realized via the delivery of a modified gene into living cells using a viral vector. Viruses are quite skilled and can invade the human body, adding their genetic material into our cells. Now researchers have learned to harness this ability to an advantage. Viruses are often used as a vehicle to deliver "good" genes into our cells, as opposed to the ones that cause disease. Viruses are modified into vectors as researchers remove disease-causing material and add the correct genetic material. In CAR T cell gene therapy, researchers often use lentiviral vector (modified from lentivirus) as the gene delivery tool. The best-known lentivirus is the Human Immunodeficiency Virus (HIV), which causes AIDS. The lentiviral vector is used because it is safe (after disabling the HIV genes), low cellular immune response, and can undergo transduction (gene modification) of both dividing and non-dividing cells. The FDA has approved the use of lentiviral vector in cancer therapy.

At present, hundreds of early phase clinical trials in gene therapy require extensive amounts of lentiviral vectors. Unfortunately, lentiviral vectors are very expensive as a result of labor and intensive manufacturing process. Lentiviral vectors currently make up about 20%-40% of the CAR T cell manufacturing cost, which contribute to the relatively high CAR T cell therapy cost ($0.5M per treatment). Lentiviral vectors are typically produced using adherent human HEK 293T cells to package multiple plasmids into viral vectors. Plasmids are small DNA molecules within a cell that can replicate independently of the chromosomes. A typical laboratory production process of lentiviral vectors is comprised of an upstream process and downstream process. In the upstream process, HEK 293T cells are cultured in a culture dish. Four plasmids, comprised of two packaging plasmids, one envelope-encoding plasmid, and one transfer plasmid, are delivered into the cells. The plasmids are packaged in the living HEK 293T cells into lentiviral vectors that carry the transfer vector responsible for gene modification of target cells. The packaged lentiviral vectors, secreted from the HEK 293T cells into the cell culture media, are harvested. In downstream process, the harvested lentiviral vectors are purified and concentrated into final product that can be used for gene modification of target cells.

Accordingly, a need remains for methods and devices to improve the production of viral vector production cells expressing viral vector components. More specifically, methods and devices are needed to improve cellular expansion, and in particular the expansion of cells, such as HEK 293T, Vero, and MDEK often used to produce virus and viral vectors, by offering improved bioreactor designs, cost-effective fabrication techniques, and improved bioreactor operating capability in order to achieve clinical application dose requirements of a selected viral vector.

SUMMARY

A 3D bioreactor for growth of viral vector producing cells, the bioreactor comprising a plurality of non-random interconnected voids, packed in 3D space in repeatable patterns, with a plurality of non-random pore openings between said voids. The bioreactor aims to achieve a maximum possible surface-to-volume ratio while the geometry is designed to maintain monolayer cell cultures, reduce or prevent high cell shear stress, cell aggregation, phenotype change, or extracellular matrix production, and is particularly suitable for the expansion of viral vector producing cells.

In one embodiment, the present invention is directed at a method for expansion of viral vector producing cells comprising:

- supplying a three-dimensional bioreactor comprising a plurality of voids having a surface area for cell expansion, said plurality of voids having a diameter D, a plurality of pore openings between said voids having a diameter d, such that D>d and wherein: (a) 90% or more of said voids have a selected void volume (V) that does not vary by more than +/−10.0%; and (b) 90% or more of said pore openings between said voids have a value of d that does not vary by more than +/−10.0%;
- seeding said three-dimensional bioreactor with viral vector producing cells;
- flowing a perfusion medium through said three-dimensional bioreactor and promoting viral vector cell expansion.

In another embodiment, the present invention is directed at a 3D bioreactor for growth of viral vector producing cells comprising a plurality of voids having a surface area for cell expansion. The plurality of voids have a diameter D of greater than 0.4 mm to 100.0 mm, a plurality of pore openings between the voids having a diameter d in the range of 0.2 mm to 10.0 mm, wherein D>d, further characterized in that: (a) 90% or more of said voids have a selected void volume (V) that does not vary by more than +/−10.0%; and (b) 90% or more of the pore openings between the voids have a value of d that does not vary by more than +/−10.0%, and the 3D bioreactor is formed from a material having a Tensile Modulus of at least 0.01 GPa.

In a still further embodiment, the present invention is directed at a 3D bioreactor for growth of viral vector producing cells comprising:

- a first and second plurality of voids having a surface area for cell expansion;
- said first plurality of voids having a diameter $D_1$, a plurality of pore openings between the first plurality of voids having a diameter $d_1$, wherein $D_1>d_1$, where 90% or more of the plurality of voids have a void volume ($V_1$) with a tolerance that does not vary by more than +/−10.0%;

said second plurality of voids having a diameter $D_2$, a plurality of pore openings between the second plurality of voids having a diameter $d_2$ wherein $D_2>d_2$, wherein 90% of the second plurality of voids have a void volume ($V_2$) with a tolerance that does not vary by more than +/−10.0%; and the values of $V_1$ and $V_2$ are different and outside of said tolerance variations such that $$[V_1+/-10.0\%]\neq[V_2+/-10.0\%].$$

The present invention also relates to a fabrication or manufacturing method of forming a 3D bioreactor comprising a plurality of voids having a surface area for viral vector cell expansion. One may therefore initially design/identify for the plurality of voids a targeted internal void volume ($V_t$) and also identify for the 3D bioreactor a targeted surface area ($SA_t$). This may then be followed by forming the 3D bioreactor with: (1) an actual void volume ($V_a$) for the one or more voids wherein $V_a$ is within +/−10.0% of $V_t$; and/or (2) an actual surface area ($SA_a$) of the 3D bioreactor wherein $SA_a$ is within +/−10.0% of $SA_t$.

DETAILED DESCRIPTION OF PREFERRED EMBODIMENTS

Figure 1:
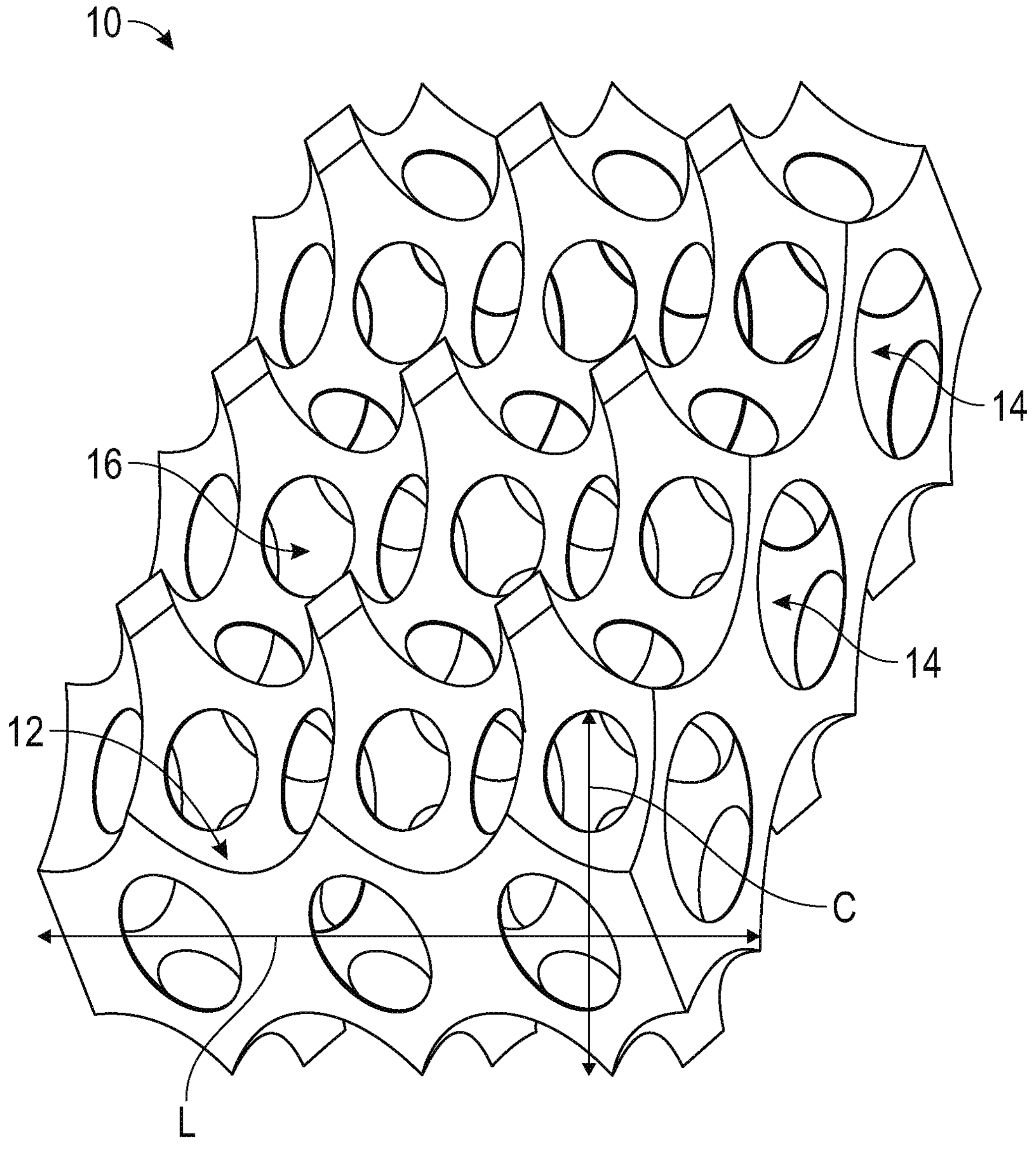
FIG. 1 illustrates a section view of the 3D bioreactor fixed-bed.

The present disclosure relates to a bioreactor design and with corresponding operating capability to achieve cell expansion of viral vector producing cells. Reference to a bioreactor herein refers to the disclosed 3D reactor in which biological and/or biochemical processes can be implemented under selected environmental and operating conditions. This includes control of one or more of the following: geometry/size of the voids, interconnected pore size between the voids and total number of voids included (determining the overall dimension of the bioreactor). In addition one may selective control surface coatings, flow characteristics through the voids within the bioreactor, pH, temperature, pressure, oxygen, nutrient supply, and/or waste removal.

The 3D bioreactor herein is one that preferably provides cellular expansion from a relatively low number of donor cells, such as viral vector producing HEK 293T cells, that also can reduce or eliminate culture passages and related MSC phenotype alterations. The 3D bioreactor's preferred fixed-bed 10 is generally illustrated in cut-away view in FIG.

1, which shows an example of a preferred packed and spherical void structure and their interconnected pores between the spherical voids.

More specifically, the bioreactor includes a continuous interconnected 3D surface area 12 that provides for the ability for the viral vector producing cells to adhere and grow as a monolayer and also defines within the bioreactor a plurality of interconnected non-random voids 14 which as illustrated are preferably of spherical shape with internal concave surfaces to maximize the surface to volume ratio. A void is understood as an open space of some defined volume. By reference to non-random it should be understood that one can now identify a targeted or selected number of voids in the 3D bioreactor that results in an actual repeating void size and/or geometry of a desired tolerance.

By reference to a continuous surface, it is understood that the expanding viral vector producing cells can readily migrate from one surface area location into another within the 3D bioreactor, and the surface does not include any random interruptions, such as random breaks in the surface or random gaps of 0.1 mm or more. Preferably, 50% or more of the surface area within the 3D bioreactor for cell expansion is a continuous surface, more preferably, 60% or more, 70% or more, 80% or more, 90% or more, 95% or more or 99% or more of the surface area within the 3D bioreactor is continuous.

In addition, the bioreactor fixed-bed 10 includes non-random interconnecting pore openings 16 as between the voids. Again, reference to non-random should be understood that one can now identify a targeted or selected number of pores for the voids, of a selected pore diameter, that results in an actual number of pores having pore diameters of a desired tolerance. The bioreactor as illustrated in cut-away view also ultimately defines a layer of non-random voids (see arrow "L") and it may be appreciated that the multiple layers of the bioreactor may then allow for identification of a plurality of such non-random voids within a column (see arrow "C").

The bioreactor may be made of biocompatible or bio-inert polymeric materials such as polystyrene, polycarbonate, acrylonitrile-butadiene-styrene (ABS), polylactic acid (PLA), polycaprolactone (PCL) used in FDM (fused deposition modeling) 3D printing technology.

Reference to biocompatible or bio-inert should be understood as a material that is non-toxic to the culturing cells. In addition, the polymeric materials for the 3D bioreactor are preferably selected from those polymers that at not susceptible to hydrolysis during cell cultivation, such that the amount of hydrolysis does not exceed 5.0% by weight of the polymeric material present, more preferably it does not exceed 2.5% by weight, and most preferably does not exceed 1.0% by weight. The bioreactor may also be made of biocompatible photosensitive materials (e.g., Pro3Dure, Somos WaterShed XC 11122, etc.) used in SLA (stereolithography) and DLP (digital light processing) 3D printing technologies.

It is preferable that the material used to fabricate the bioreactor is not degradable in aqueous medium and can provide a mechanical stable structure to tolerate aqueous medium flow during cell expansion. It is preferable that the material and manufacturing process can result a solid and smooth interconnected surface area for monolayer cell expansion. By reference to a solid surface, it should be understood that the surface is such that it will reduce or prevent penetration or embedding by the culturing viral vector producing cells, which typically have a diameter of about 20 microns to 100 microns. Preferably, the 3D bioreactor herein is one that has a surface that has a surface roughness value (Ra), which is reference to the arithmetic average of the absolute values of the profile height deviations from the mean line, recorded within an evaluation length. Accordingly, it is contemplated herein that Ra of the 3D bioreactor surface will have a value of less than or equal to 20 μm, more preferably, less than or equal to 5 μm.

The 3D bioreactor herein is also preferably one that is formed from material that indicates a Shore D Hardness of at least 10, or in the range of 10-95, and more preferably in the range of 45-95. In such regard, it is also worth noting that the 3D bioreactor herein is one that does not make use of a hydrogel type structure, which may be understood as a hydrophilic type polymeric structure, that includes some amount of crosslinking, and which absorbs significant amounts of water (e.g., 10-40% by weight). It is also worth noting that the 3D bioreactor herein is one that preferably does not make use of collagen, alginate, fibrin and other polymers that cells can easily digest and undergo remodeling.

Furthermore, the 3D bioreactor herein is preferably one that is made from materials that have a Tensile Modulus of at least 0.01 GPa. More preferably, the Tensile Modulus has a value that is in the range of 0.01 GPa to 20.0 GPa, at 0.01 GPa increments. Even more preferably, the Tensile Modulus for the material for the 3D bioreactor is in the range of 0.01 GPa to 10.0 GPa or 1.0 GPa to 10 GPa. For example, with respect to the earlier referenced polymeric materials suitable for manufacture of the 3D bioreactor herein, polystyrene indicates a Tensile Modulus of about 3.0 GPa, polycarbonate at about 2.6 GPa, ABS at about 2.3 GPa, PLA at about 3.5 GPa and PCL at about 1.2 GPa.

The 3D bioreactor design herein with such preferred regular geometric characteristics and continuous surface area is preferably fabricated by additive manufacturing technologies, such as FDM, selective laser sintering (SLS), stereolithography (SLA), digital light processing (DLP) 3D printing technologies, etc., according to computer generated designs made available by, e.g., a SolidWorks™ computer-aided design (CAD) program.

By way of preferred example, the process utilizing SolidWorks™ to create the 3D bioreactor design is described below. A computer model for the bioreactor negative is initially created. More specifically, what may therefore be described as a 3D bioreactor negative was created, e.g., using packed 6.0 mm diameter spheres that overlap to create 1.0 mm diameter connecting pores between spheres. Of course, other possible dimensions are contemplated within the broad context of this disclosure.

Figure 1A:
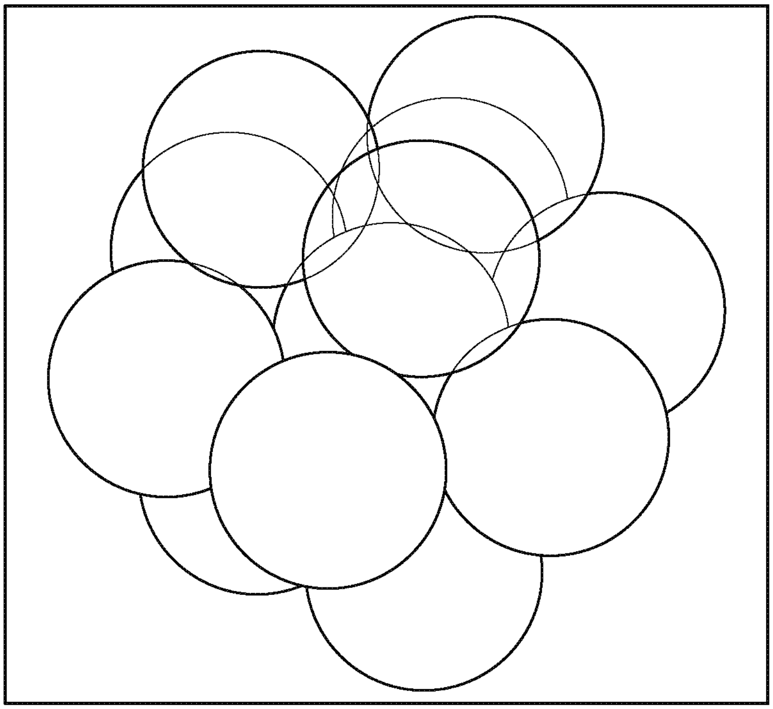
FIG. 1*a* illustrates a unit negative model of the bioreactor that shows the overlapping of the neighborhood spheres.

The spheres are preferably organized in a hexagonal close packed (HCP) lattice to create an efficiently (or tightly) packed geometry that results in each sphere surrounded by 12 neighborhood spheres. A unit cell of this exemplary geometry is shown in FIG. 1*a*. More specifically, in FIG. 1*a* there is a unit cell of the HCP lattice where the top three spheres are displayed as translucent to show the 6 radial overlapping areas between the neighborhood spheres. The pores are formed at these overlapping areas. Preferably, the maximum number of pores is 12 to optimize packing. The minimum pore number is 2 in order to allow a perfusion medium through the voids of the 3D bioreactor. Perfusion medium herein is typically a cell culture medium such as a liquid or gel designed to support the growth of cells. A typical culture medium is artificial or synthetic media composed of a complement of amino acids, vitamins, inorganic salts, glucose, and serum as a source of growth factors, adhesion factors, hormones, lipids and minerals. The perfusion medium can also be other synthetic media such as serum-free media, protein-free media or chemically defined media. The perfusion medium can also be natural media such as blood, plasma, amniotic fluid, etc.

Accordingly, at least 90.0% to 100% of the voids present in the 3D bioreactor have at least 2 pore openings per void. More preferably, at least 90.0% to 100% of the voids in the 3D bioreactor have 8-12 pore openings per void. In one particularly preferred embodiment, at least 90.0% to 100% of the voids in the 3D bioreactor have 12 pore openings per voids between adjacent voids within the plurality of voids present, and more preferably, there are 8-12 interconnected pore openings between the adjacent voids, and in one particularly preferred embodiment, there are 12 pore openings between the adjacent voids.

Figure 1B:
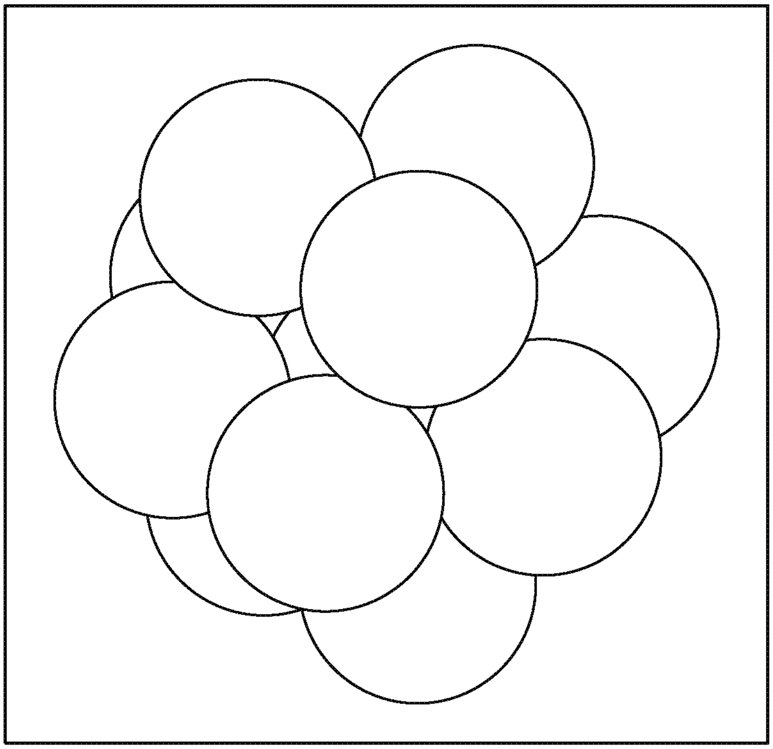
FIG. 1*b* illustrates a unit negative model with each sphere surrounded by 12 identical neighborhood spheres.
Figure 1C:
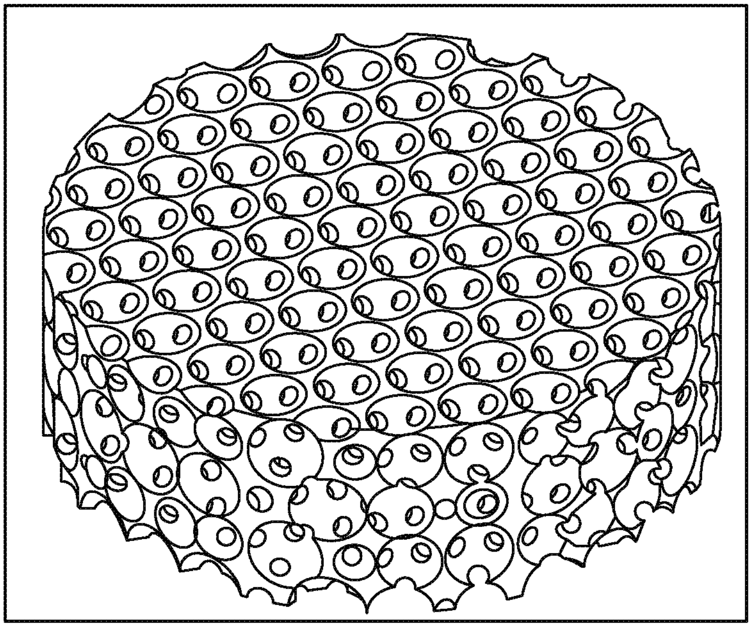
FIG. 1*c* illustrates a 3D bioreactor fixed-bed geometry showing an interconnected void system.
Figure 1D:
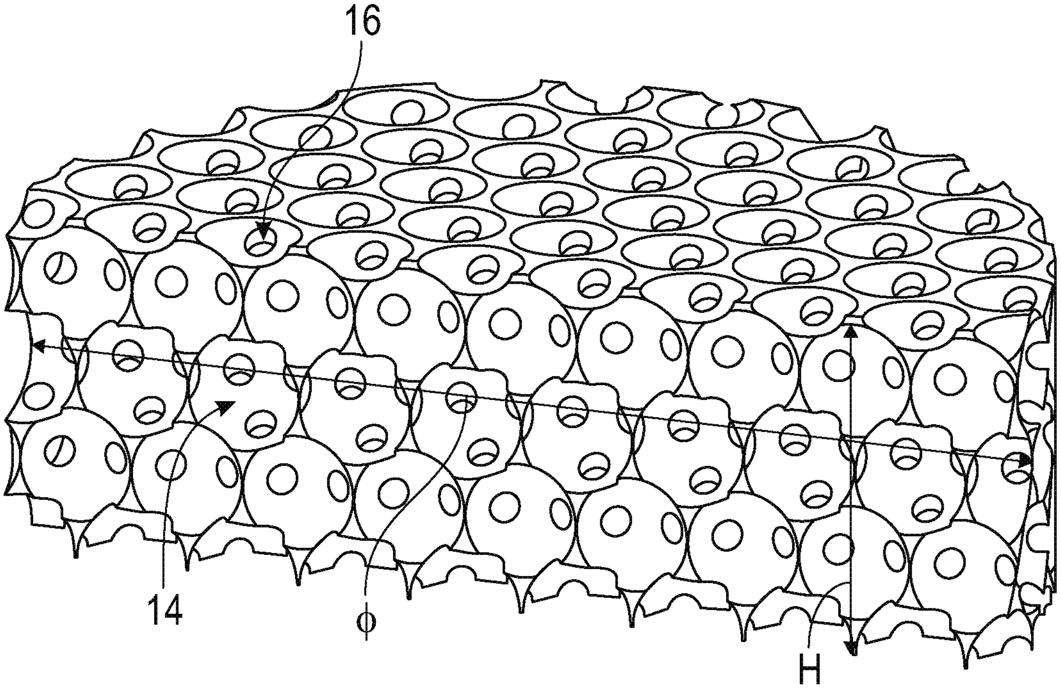
FIG. 1*d* illustrates a 3D bioreactor fixed-bed geometry in cross-sectional view.

In FIG. 1*b*, all spheres of the unit are illustrated. The bioreactor geometry is then preferably created by reversing the negative model to create the positive model comprising an interconnected spherical void system shown in FIG. 1*c*. Moreover, in FIG. 1*d* one can see the 3D bioreactor again in cross-sectional view providing another illustration of the interconnected voids shown in cut-away view at 14 with regular geometric characteristics (substantially the same control of void volume as described above) and the corresponding interconnected pore openings 16.

Figure 1E:
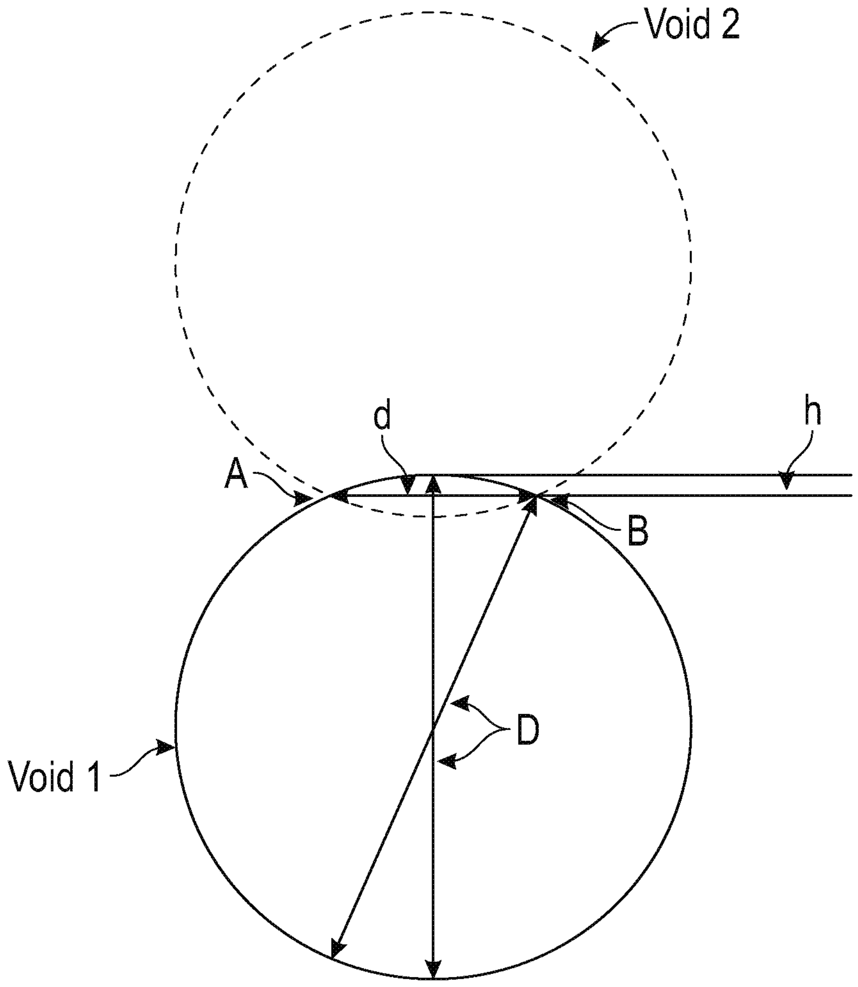
FIG. 1*e* illustrates in 2D view the identified spherical voids of a 3D bioreactor, and their overlapping areas to form interconnected pores between the spherical voids.

In the preferred regular geometric 3D bioreactor described above, one can identify a relationship as between the void diameter and interconnected pore diameter. Attention is directed to FIG. 1*e*. For this preferred geometry, Spherical Void 1 is represented by a solid circle, diameter is D (indicated by the arrows). Diameter "D" may therefore be understood as the longest distance between any two points on the internal void surface. Spherical Void 2 is represented by a dash circle and would also have diameter D (not shown). Spherical Void 2 is one of the 12 of neighborhood voids of Spherical Void 1. Due to the overlap between the neighborhood voids, it forms interconnected pores between the spherical voids, with the diameter of "d" as also indicated by the generally horizontal arrow. Diameter "d" may therefore be understood as the longest distance between any two points at the pore opening. The total 3D spherical surface area of the void is $SA_{void}=4\times\pi(D/2)^2$. The surface area between A and B, called $S_{cap}=\pi\times D\times h$, where $$h=\frac{D-\sqrt{D^2-d^2}}{2}.$$

The useful void surface for a given void in the 3D bioreactor would be $SA_u=S_{Avoid}-[12\times S_{cap}]$.

The smaller the void diameter D, the larger the number of voids can be packed into a set 3D space (volume), and therefore results larger overall cell culture surface. However, to minimize or prevent cell aggregation (which as discussed herein can inhibit cell growth and induce cell phenotype change), the minimal diameter of the pores d=0.2 mm for this geometry. The diameter of the pores d may fall in the range of 0.2 mm to 10 mm and more preferably 0.2 mm to 2.0 mm. Most preferably, d≥0.5 mm and falls in in the range of 0.5 mm to 2.0 mm.

If D=0.40 mm or less, the computed $SA_u$ is less than 0 when d=0.2 mm, which leads to an impossible structure therefore, D has to be >0.4 mm for this 3D bioreactor geometry. However, D can have a value between 0.4 mm to 100.0 mm, more preferably, 0.4 mm to 50.0 mm, and also in the range of 0.4 mm to 25.0 mm. One particularly preferred value of D falls in the range of 2.0 mm to 10.0 mm. Spherical voids with a relatively large value of D may reduce the objective of increasing cell culture surface area as much as possible within a same bioreactor volume. Accordingly, for the preferred geometry illustrated in FIG. 1E, D>0.4 mm (the diameter of the void) and d>0.20 mm (the diameter of the pores). It is also worth noting that with respect to any selected value of diameter D for the voids in the range of 0.4 mm to 100.0, and any selected value of diameter d for the pores in the range of 0.2 mm to 10.0 mm, the value of D is such that it is greater than the value of d (D>d).

It can now be appreciated that the 3D bioreactor herein can be characterized with respect to its non-random characteristics. Preferably, all of the voids within the 3D bioreactor are such that they have substantially the same volume to achieve the most efficient 3D space packing and offer the largest corresponding continuous surface area. With respect to the total number of interconnected voids present in any given 3D bioreactor, preferably, 90.0% or more of such voids, or even 95.0% or more of such voids, or even 99.0% to 100% of such voids have a void volume (V) whose tolerance is such that it does not vary by more than +/−10.0%, or +/−5.0%, or +/−2.5% or +/−1.0%, or +/−0.5% or +/−0.1%. It should be noted that while the voids in FIG. 1 are shown as generally spherical, other voids geometries are contemplated. The diameter of voids are chosen to minimize or avoid cell aggregation and to provide maximum useful surface area for cell culturing.

Another non-random characteristic of the 3D bioreactor herein are the pore openings between the voids, having a diameter d (see again FIG. 1*e*). Similar to the above, 90.0% or more of the pore openings, or even 95.0% or more of the pore openings, or even 99.0% to 100% of the pore openings between the voids, indicate a value of d whose tolerance does not vary more than +/−10.%, or +/−5.0%, or +/−2.5% or +/−1.0%, or +/−0.5% or +/−0.1%.

It can therefore now by appreciated that the 3D bioreactor herein for growth of cells comprises a surface area for cell expansion, a plurality of voids having a diameter D (the longest distance between any two points on the internal void surface), a plurality of pore openings between said voids having a diameter d (the longest distance between any two points at the pore opening), where D>d. In addition, 90% or more of the voids have a void volume (V) that does not vary by more than +/−10.0%, and 90% or more of the pore openings have a value of d that does not vary by more than +/−10.0%.

In addition, the 3D bioreactor herein for growth of viral vector producing cells can include a first plurality of voids having a diameter $D_1$, a plurality of pore openings between said first plurality of voids having a diameter $d_1$, wherein $D_1>d_1$, where 90% or more of the first plurality of voids have a void volume ($V_1$) with a tolerance that does not vary by more than +/−10.0%. Such 3D bioreactor may also have a second plurality of voids having a diameter $D_2$, a plurality of pore openings between said second plurality of voids having a diameter $d_2$ wherein $D_2>d_2$, wherein 90% of the second plurality of voids have a void volume ($V_2$) with a tolerance that does not vary by more than +/−10.0%. The values of $V_1$ and $V_2$ are different and outside of their tolerance variations. Stated another way, the value of $V_1$, including its tolerance of +/−10.0% and the value of $V_2$, including its tolerance of +/−10.0%, are different, or $[V_1+/-10.0\%]\neq[V_2+/-10.0\%]$.

The radius of curvature (Rc) of the surface within the voids is therefore preferably 1/0.5(D), or 1/0.2 mm=5 $mm^{-1}$ or lower. Preferably, Rc may have a value of 0.2 $mm^{-1}$ to 1.0 $mm^{-1}$, which corresponds to a value of D of 10.0 mm to 2.0 mm. A high curvature (large Rc) surface provides a significantly different environment than the typical monolayer 2D culture, which may also induce cell phenotype changes.

Viral vector producing cells are preferably seeded on the interconnected spherical void surfaces of the 3D bioreactor. Such 3D structure is preferably scalable and is able to provide a relatively high surface-to-volume ratio for the expansion of relatively large number of cells with a relatively small footprint. The surface area-to-volume ratio is also preferably determined by the diameter of the spherical voids. The smaller is the diameter, the higher is the surface area-to-volume ratio. Preferably, the voids provide a relatively "flat" surface (i.e., low radius of curvature 1.0 $mm^{-1}$) for growth of cells having a size of 20 μm to 100 μm and also to reduce or avoid cell aggregation. In addition, as alluded to above, cell aggregation is also reduced or avoided by controlling the diameter d of the interconnected pores, which diameter is preferably at least 500 μm, but as noted, any size greater than 200 μm.

Figure 2:
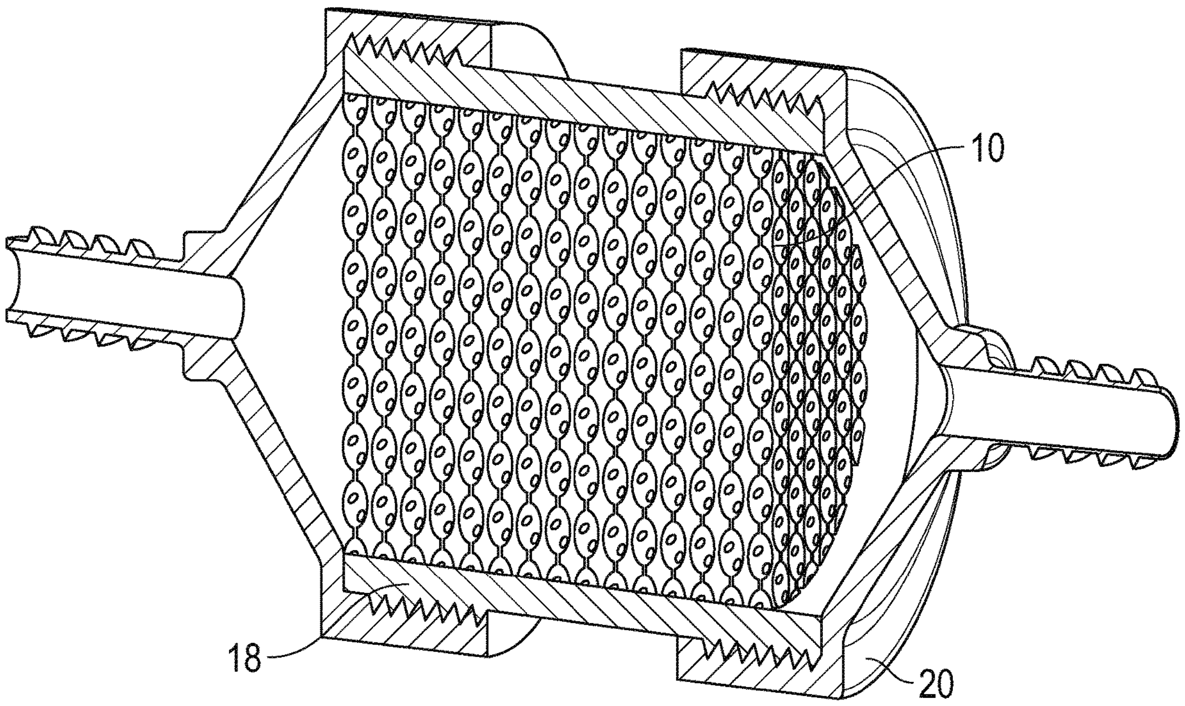
FIG. 2 illustrates a 3D bioreactor fixed-bed positioned in a housing with inlet and outlet for fluid perfusion.
Figure 3:
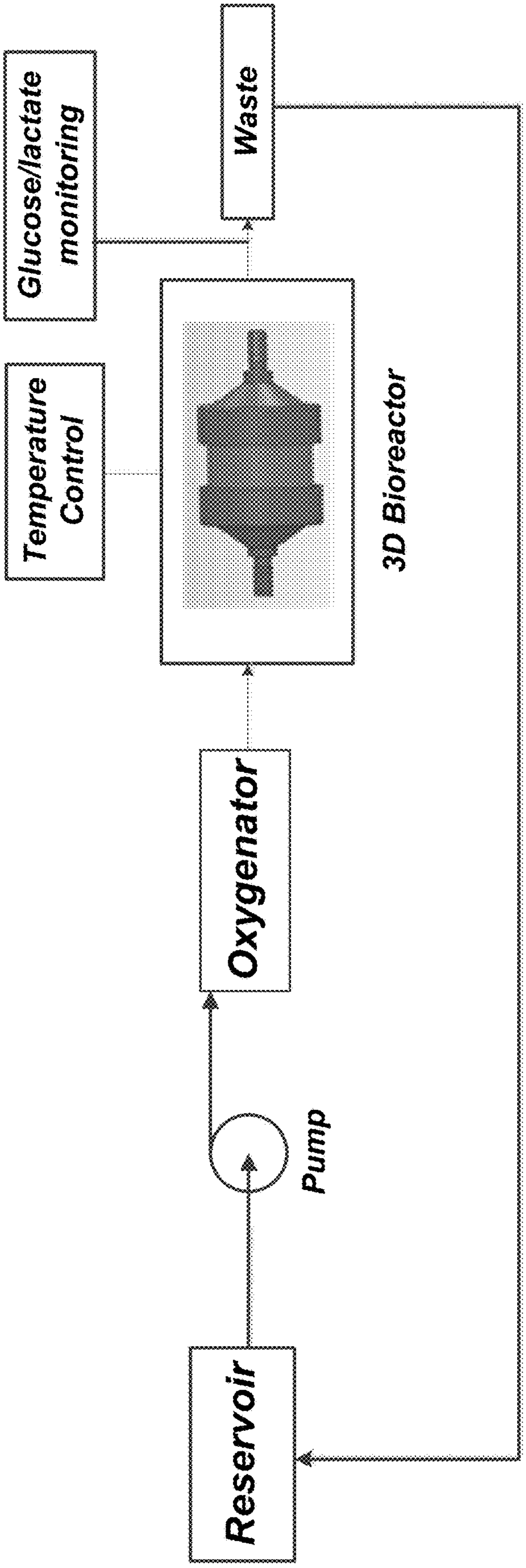
FIG. 3 illustrates a typical 3D bioreactor perfusion system.

The bioreactor fixed-bed 10 may therefore preferably serve as a single-use 3D bioreactor as further illustrated in FIG. 2. More specifically, the bioreactor 10 may be positioned in a housing 18 and then placed in the inlet and outlet compartment 20 for which inflow and outflow of fluid may be provided. Preferably, the bioreactor 10, housing 18, and the inlet and outlet compartment 20 can be fabricated as a single component using Additive Manufacturing technology. As shown in FIG. 3, the bioreactor 10 in housing 18 and inlet and outlet compartment 20 may become part of an overall 3D bioreactor system for cellular expansion. More specifically, the 3D bioreactor is preferably positioned within a perfusion system which delivers a viral vector producing cell culture medium and oxygen through the 3D bioreactor for promoting such cell growth. Multiple passage cell expansion methods used in 2D T-flask can also be directly applied to the 3D bioreactor except a 3D bioreactor has the cell culture area equivalent to 10s, 100s, or 1000s of T-flasks. Besides multiple passage cell expansion, a one-step expansion from a low number of donor cells to a clinically relevant number of cells is contemplated thus eliminating the multiple-passaging problem that induces MSC phenotype changes during expansion.

As may now be appreciated, the 3D bioreactor herein offers a relatively large surface-to-volume ratio depending upon the diameter of the interconnected voids. By way of example, a conventional roller bottle defining a cylinder of 5 cm diameter and 15 cm height, provides a cell growth surface area of 236 $cm^2$. If the same volume is used to enclose the 3D bioreactor herein with 2.0 mm diameter interconnected voids, a total of 44,968 spherical voids can be packed into the space, which can provide a matrix with about 5,648 $cm^2$ surface area, an almost 24-fold larger than the roller bottle surface area. In addition, while the roller bottle can only harvest around $9.4 \times 10^6$ cells, the equivalent volume 3D bioreactor herein is contemplated to harvest $2.2 \times 10^8$ cells.

At least one unique feature of the 3D bioreactor herein in comparison with hollow-fiber or microcarrier-based bioreactors is the ability to provide a large interconnected continuous surface instead of fragmented surfaces. Continuous surfaces within the 3D bioreactor herein are therefore contemplated to enable cells to more freely migrate from one area to another. The cells can then proliferate locally and at the same time gradually migrate out of the region to avoid cell-cell contact inhibition and differentiation. Using the perfusion system shown in FIG. 3, it is contemplated that one can readily create a gradient of nutrition or cell signals inside the bioreactor to induce cell migration into an open space while proliferating (as in a wound healing process).

The 3D bioreactor herein is also contemplated to allow one to seed a relatively low number of viral vector producing cells relatively evenly across the matrix surface. It is contemplated that the number of seeding cells can fall in the range of 30 to 3000 cells per square centimeter of useful void surface area, depending upon the size of the 3D bioreactor. Cells distributed in a 3D space within the 3D bioreactor herein can have a relatively large intracellular 2D separation to avoid direct cell-cell contact. At the same time it is possible to have a relatively short 3D separation distance (e.g., when cells reside on a spherical surface of opposite direction) enabling signals from nearby cells to be received.

In conjunction with the preferred 3D printing technology noted herein for preparation of the 3D bioreactor, computational fluid dynamics (CFD) can now be used to simulate the medium flow inside the bioreactor and estimate the flow rate and shear stress at any location inside the 3D interconnected surface, and allow for optimization to improve the cell culture environment. More specifically, CFD was employed to simulate the flow characteristics through the 3D interconnected voids of the bioreactor herein and to estimate the distribution of: (1) flow velocity; (2) pressure drop; and (3) wall shear stress. It may be appreciated that the latter parameter, shear stress, is important for cell expansion. A reduction in shear stress can reduce or prevent shear induced cell differentiation.

A small-scale (to increase computer simulation speed) cylindrical 3D bioreactor with a diameter of 17.5 mm, height of 5.83 mm, void diameter of 2 mm, and pore diameter of 0.5 mm was used in the simulations reported below. In this case, the diameter (1=17.5 mm) to height (H=5.83 mm) ratio of the bioreactor is 3:1 (FIG. 1*d*), which is a preferable ratio to reduce the gradient of nutrition and oxygen between the inlet and outlet of the bioreactor. Based on the cell density available on the fixed-bed spherical surface the oxygen and nutrition consumption rates were estimated, and how often the cell culture media needed to be replaced (i.e., the volume flow rate) was determined. An overall linear flow rate of 38.5 μm/sec was assumed in this simulation. Using 38.5 μm/sec rate laminar flow as the input to the 3D bioreactor, the CFD results are shown in FIGS. 4-6.

FIGS. 4*a*, 4*b*, 4*c* and 4*d* show the flow velocity profile throughout the small-scale cylindrical 3D bioreactor. FIG. 4*e* indicates the scale of flow rate. More specifically, FIG. 4*a* indicates the flow rate distribution viewed from the side of the bioreactor. The flow passes each spherical voids through the pores along the flow direction. The white/gray areas in the figures are the solid regions between the spherical voids with no fluid flow. By comparing with the colored velocity scale bar in FIG. 4*e*, FIG. 4*a* indicates that the flow rate at the pores along the flow direction achieve the maximum flow rate of 200 μm/s to 240 μm/s. In contrast, the flow rates near the spherical surface reduce to a minimum of 0.06 μm/s to 19.0 μm/s, which will significantly reduce the flow caused shear stress to cells reside on the spherical surface.

Figure 4A:
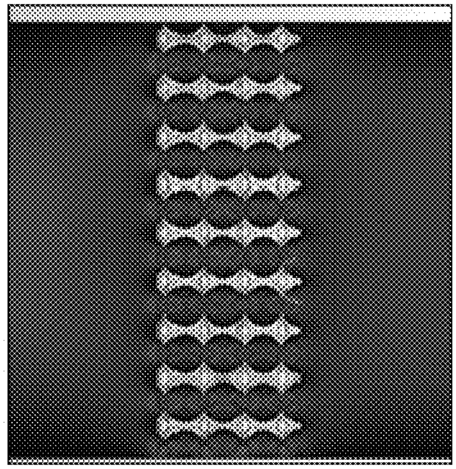
FIGS. 4*a*, 4*b*, 4*c* and 4*d* show flow rate profiles through a 3D bioreactor.
Figure 4B:
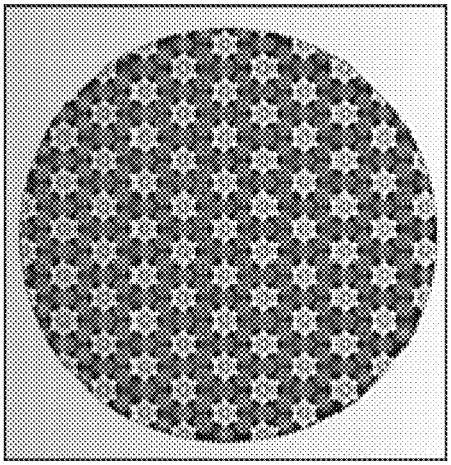

FIG. 4*b* indicates the velocity profile viewed from the top of the bioreactor through a center cross-section of the 3D structure. Again the image shows that the maximum rates are at each center of the pores of the spherical voids along the flow direction. This maximum rate is again in the range of 200 μm/s to 240 μm/s. The flow rate near spherical surface is again low and has a value of 0.06 μm/s to 19.0 μm/s.

Figure 4C:
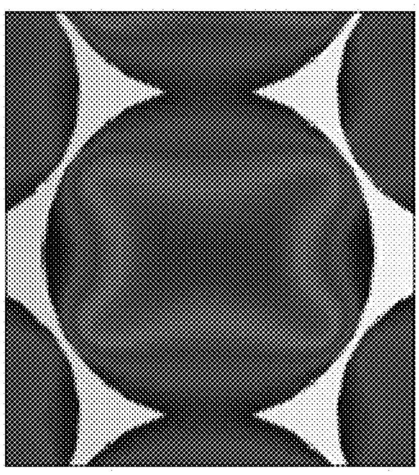
Figure 4D:
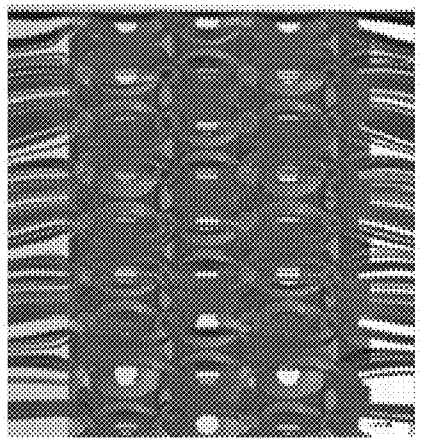
Figure 4E:
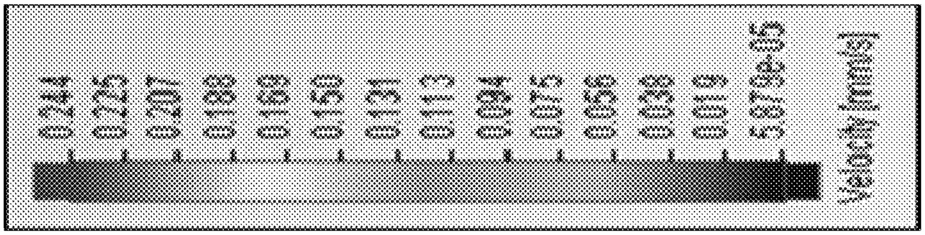
FIG. 4*e* indicates the scale of flow rate through a 3D bioreactor.

FIG. 4*c* indicates the velocity profile of an individual sphere void showing flow passing through the radial interconnected pores. FIG. 4*c* therefore provides a useful illustration of the flow distribution inside a spherical void. The high flow rate is at the central empty space of a void where there are no cells and is at a level of 200 μm/s to 240 μm/s. The cells reside on the concaved void surface where the flow rate is reduced and where the flow rate is again at a level of 0.06 μm/s to 19.0 μm/s. This unique structure can therefore shield cells from exposure to relatively high flow stress. This is another distinct advantage of the 3D bioreactor described herein over, e.g., micro-carrier based reactors, where cells are grown on the outside surface surfaces of 300 μm to 400 μm diameter microbeads with convex spherical surfaces that are suspended in a cell culture medium and stirred in a bioreactor to deliver nutrition and oxygen to the cells. Cells residing on such convex spherical surfaces can be exposed to relatively large shear stress to 0.1 Pa, which is known to affect cellular morphology, permeability, and gene expression. FIG. 4*d* indicates the flow trajectory through the side pores along the flow direction, indicating that the 3D bioreactor herein provides a relatively uniform flow pattern to provide nutrients and oxygen throughout.

Accordingly, the maximum linear flow rate computed inside the preferred 3D bioreactor is 200 μm/s to 240 μm/s which occurs at the 0.5 mm diameter interconnected pores between 2.0 mm diameter voids along the flow direction. As shown in FIGS. 4*a*-4*e* while the flow is preferentially in the central direction along the flow, there is still flow (~19.0 μm/sec) near the spherical surface to allow nutritional supply to the cells residing on the spherical surface. Therefore, it is contemplated that the cells are able to reside anywhere throughout the structure and thrive in any location because nutrients can be supplied both through flow convection and diffusion throughout the 3D bioreactor structure.

Figure 5C:
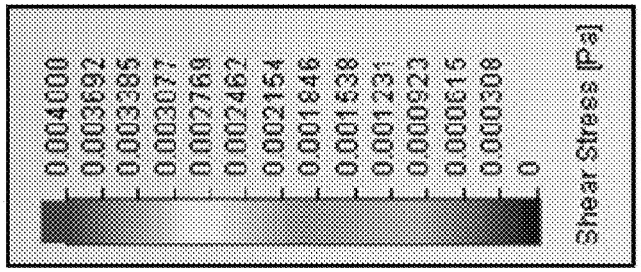
FIG. 5*c* indicates a scale of shear stress in unit Pa.
Figure 5B:
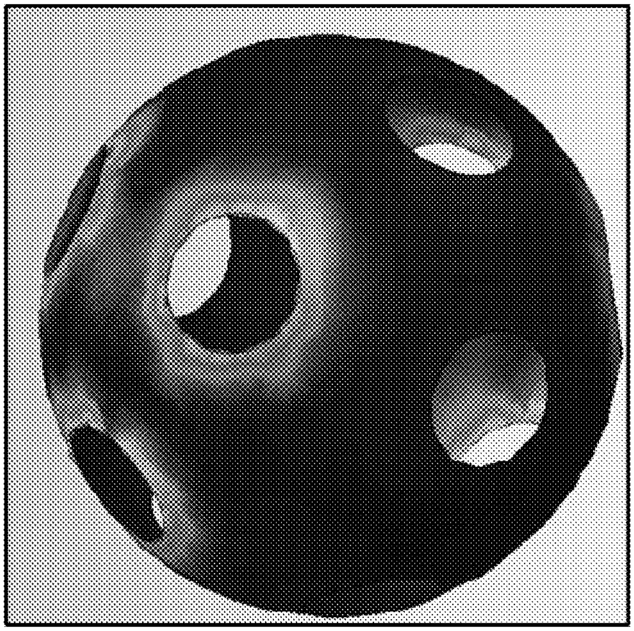
FIGS. 5*a* and 5*b* illustrate the distribution of surface shear stress in a 3D bioreactor.
Figure 5A:
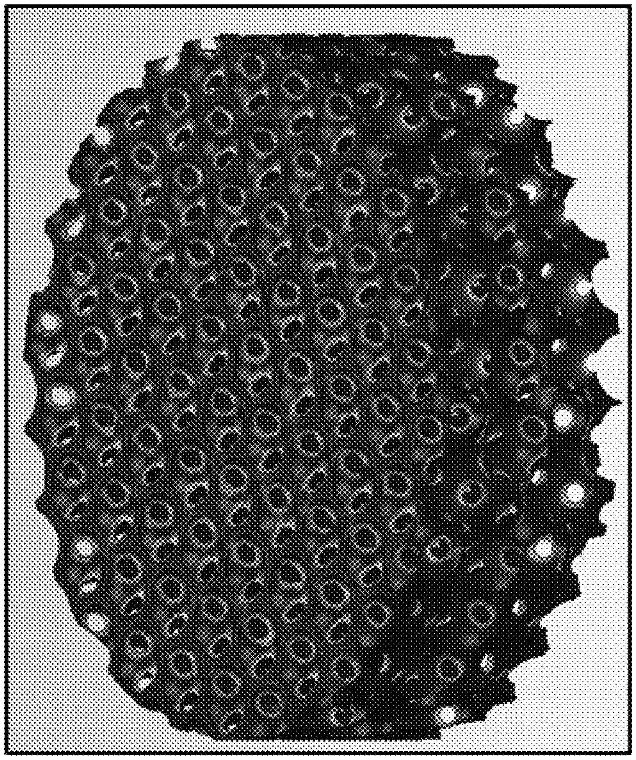

FIGS. 5*a* and 5*b* show the distribution of surface shear stress throughout the cylindrical 3D bioreactor described above as well as on a single spherical void surface. FIG. 5*c* indicates the scale of shear stress in units of Pa. The highest shear stress was observed on the edges of the interconnected pores. This is due to the higher flow rates at these locations. However, the majority of the useful spherical surface area within the bioreactor indicates a shear stress of less than $3\times10^{-4}$ Pa, which may be understood as 90% or more of the surface area of the bioreactor. This provides for cell proliferation, without shear induced differentiation. In addition, even the maximum shear stress of $4.0\times10^{-3}$ Pa, is believed to be lower than the average shear stress that cells experience when cultured in hollow fiber based bioreactors, wave bioreactors, and micro-carrier based bioreactors. Therefore, the 3D bioreactor herein is contemplated to provide a relatively lower shear stress environment for cell growth in comparison to existing cell expansion bioreactors. See, e.g., *Large-Scale Industrialized Cell Expansion: Producing The Critical Raw Material For Biofabrication Processes*, A. Kumar and B. Starly, Biofabrication 7(4):044103 (2015).

Figure 6B:
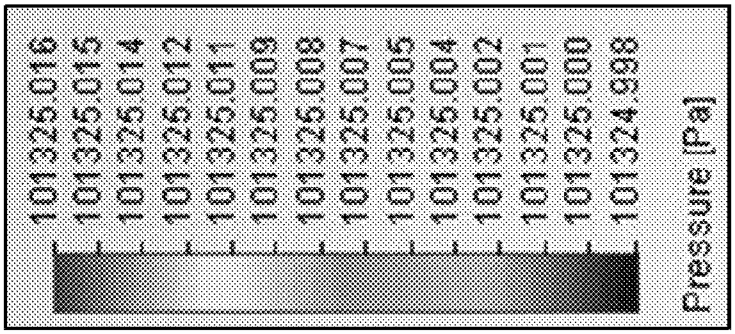
FIG. 6*b* indicates a scale of pressure.
Figure 6A:
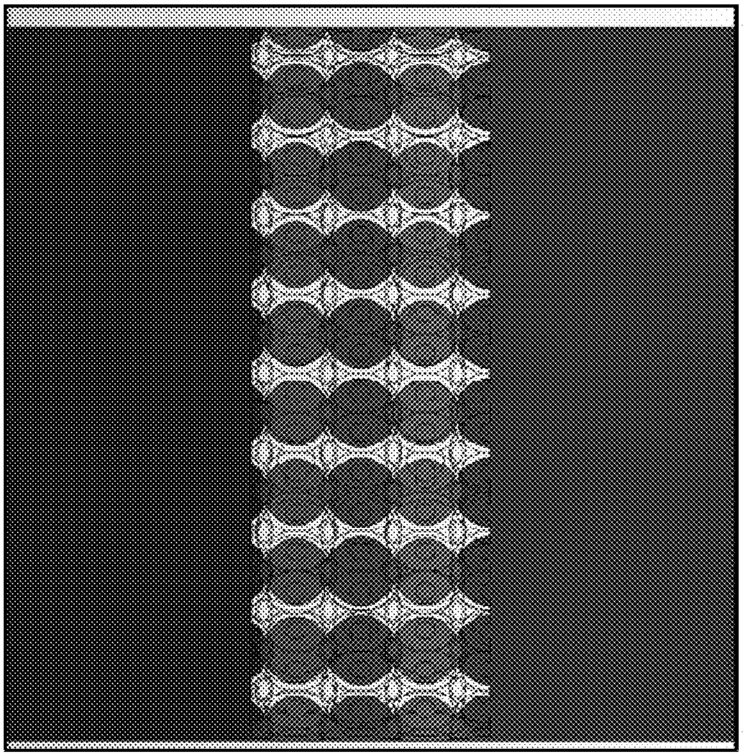
FIG. 6*a* illustrates the pressure drop (gradient) along the flow direction in a cylindrical 3D bioreactor.

FIG. 6*a* illustrates the pressure drop along the flow direction from bottom to the top of the cylindrical 3D bioreactor described above. FIG. 6*b* provides the applicable scale of pressure. The figure indicates that the overall pressure drop between the inlet and outlet of the bioreactor is less than or equal to 1.0 Pa. The pressure drop may therefore fall in the range of 0.1 Pa up to 1.0 Pa. In other words, cells near the inlet and outlet of the bioreactor will not experience significant differences in pressure. The low gradient of pressure suggests that such design will also produce a small gradient (or difference) in nutrition/metabolites concentrations between the inlet and outlet of the bioreactor. The low gradient is due to the design of the bioreactor such that the diameter Φ is larger than the height H while the total bioreactor volume remains the same. This is superior to the hollow fiber bioreactor. It is difficult to fabricate a hollow fiber bioreactor with Φ>H ratio to reduce the gradient of nutrition/metabolites between the inlet and outlet of the bioreactor.

A comparison was also made for the same total volume cylindrical 3D bioreactor with different aspect ratios (i.e. Φ:H ratio, Φ): overall diameter of the bioreactor fixed-bed, H: overall height of the bioreactor fixed-bed). See FIG. 1*d*. As shown in Table 1, for the same volume flow rate (volume flow rate=cross area of flow×linear velocity), the linear velocity increases significantly for a bioreactor with a low Φ:H ratio. The increase of linear velocity also increases the surface shear stress, pressure drop, as well as the gradient of nutrition/metabolites concentrations between the inlet and outlet, which would have an unfavorable effect for cell expansion. The disclosed fixed-bed 3D bioreactor is therefore preferably designed into a Φ:H ratio structure, e.g., a Φ:H ratio in the range of greater than 1:1 and up to 100:1 Preferably, the Φ:H ratio is greater than 1:1 and up to 10:1.

TABLE 1

Flow Rate Comparison For 3D Bioreactor With Different Aspect Ratios

| # | Ratio (Φ:H) | Diameter (Φ) (cm) | Height (H) (cm) | Flow Rate (μm/sec) |
|---|---|---|---|---|
| 1 | 3:1 | 10.5 | 3.5 | 38.5 |
| 2 | 1:1 | 7.5 | 7.5 | 75.4 |
| 3 | 1:3 | 5 | 15 | 169.8 |

Figure 7B:
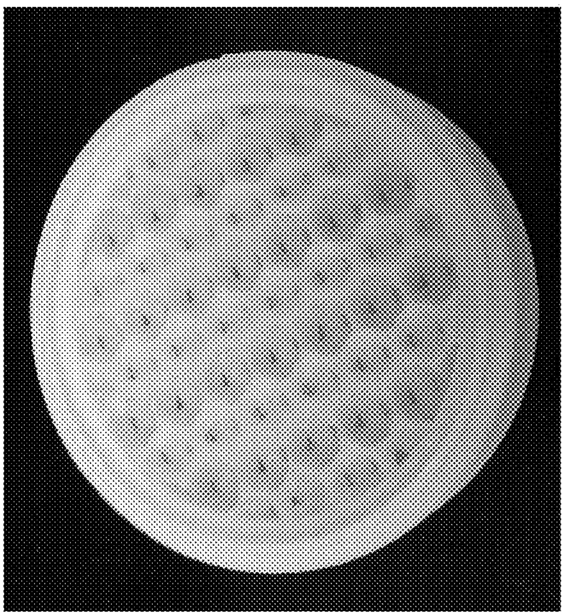
FIG. 7*b* illustrates the 3D bioreactor fixed-bed together with a bioreactor chamber.
Figure 7D:
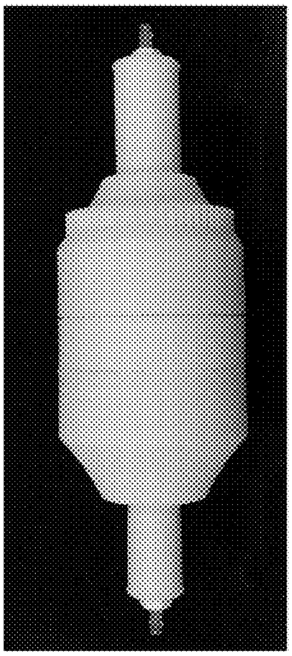
FIG. 7*d* illustrates an assembled 3D bioreactor.
Figure 7A:
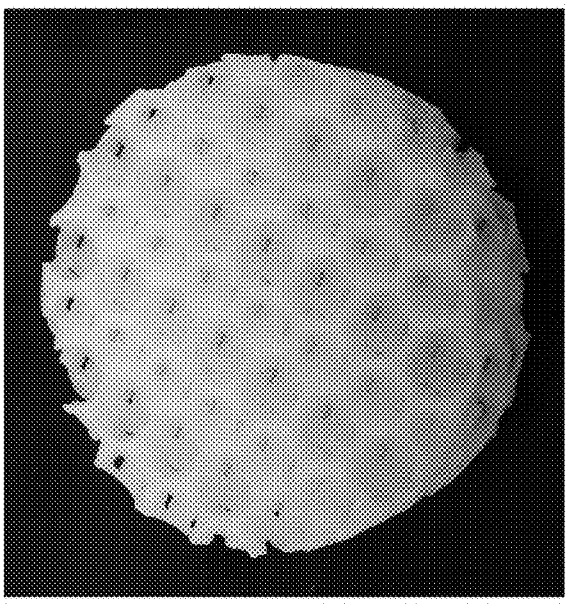
FIG. 7*a* illustrates a 3D bioreactor fixed-bed generated by FDM 3D printing.
Figure 8:
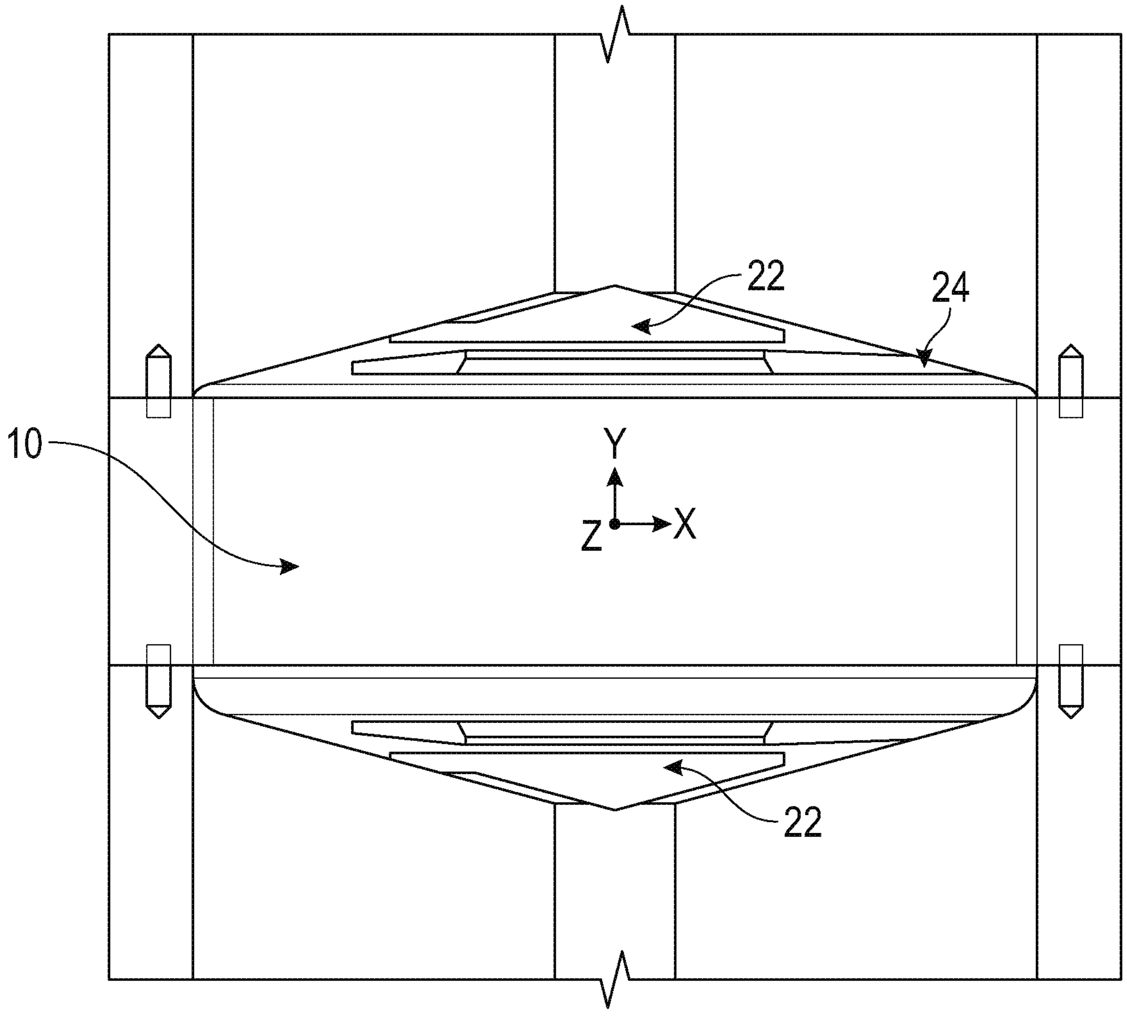
FIG. 8 illustrates two fluid distributors placed at the inlet and outlet of the 3D bioreactor to approach a laminar flow.

FIG. 7*a* illustrates a 3D bioreactor fixed-bed part generated by FDM 3D printing with interconnected 6 mm diameter voids and 1 mm interconnected pores. This 3D bioreactor was printed with ABS filament. The diameter (Φ) and height (H) of this particular 3D bioreactor is 4.28 cm and 1.43 cm respectively. Accordingly the Φ:H ratio is 3:1. There are about 134 interconnected open-voids included in the fixed-bed. The total interconnected continuous spherical surface area $SA_u$ for cell culturing is about 152 $cm^2$. The inlet and outlet wall and fluid distributor 22 at the inlet and outlet (FIG. 8) provides an additional 88 $cm^2$ surface area for cell culturing. In other words, there is about 240 $cm^2$ total useful surface area in the 3D bioreactor for cell attachment. The fluid distributor can improve the laminar flow through the bioreactor. The fluid distributor is optional if the Reynolds number is <2100 or in the range of greater than 0 up to and not including 2100.

Figure 7C:
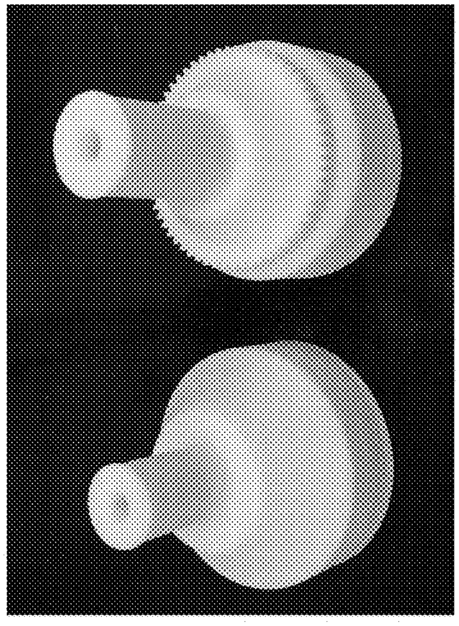
FIG. 7*c* illustrates the inlet and outlet of a 3D bioreactor.
Figure 7F:
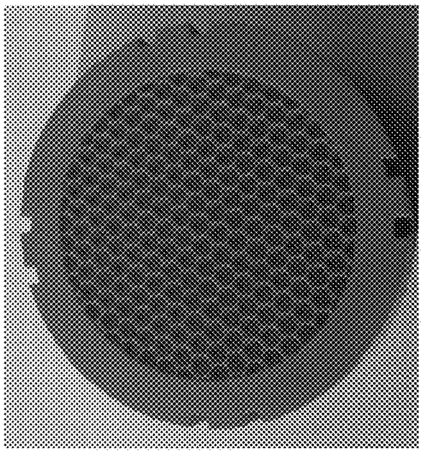
FIG. 7*f* illustrates a 3D bioreactor fixed bed generated by DLP 3D printing.
Figure 7E:
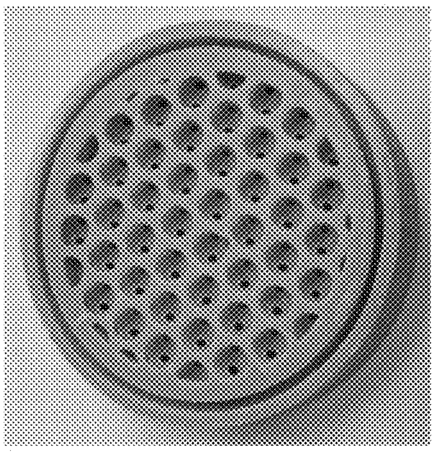
FIG. 7*e* illustrates a 3D bioreactor fixed-bed generated by SLA 3D printing.

FIG. 7*b* shows that the fixed-bed of the 3D bioreactor was solvent bound into a bioreactor chamber. This will seal the gaps between the fixed-bed and the chamber wall, which will force the perfusion cell culture medium to pass through the interconnected pores instead of through those gaps. Preferably, the fixed-bed and chamber is printed together as an integrated part to increase the manufacturing efficiency. FIG. 7*c* illustrates the inlet and outlet of the bioreactor. They are designed geometrically to promote a laminar flow through the fixed-bed. The inlet of the bioreactor optionally contains a built-in rotation gear, which may be coupled to a stepper motor to control the rotation of the bioreactor for uniform cell seeding (see below). The integrated bioreactor is shown in FIG. 7*d* and is able to connect to ⅛ inch tubing to conduct the fluid flow. Alternatively, the inlet and outlet can be made for repeated usage, where only the inside bioreactor fixed bed is disposable. Also shown in FIG. 7*e* is a 3D bioreactor fixed bed produced by SLA 3D printing having a 6.0 mm void and a 1.0 mm pore. FIG. 7*f* is a 3D bioreactor fixed bed using DLP 3D printing having a 3.0 mm void and a 0.5 mm pore.

Figure 9:
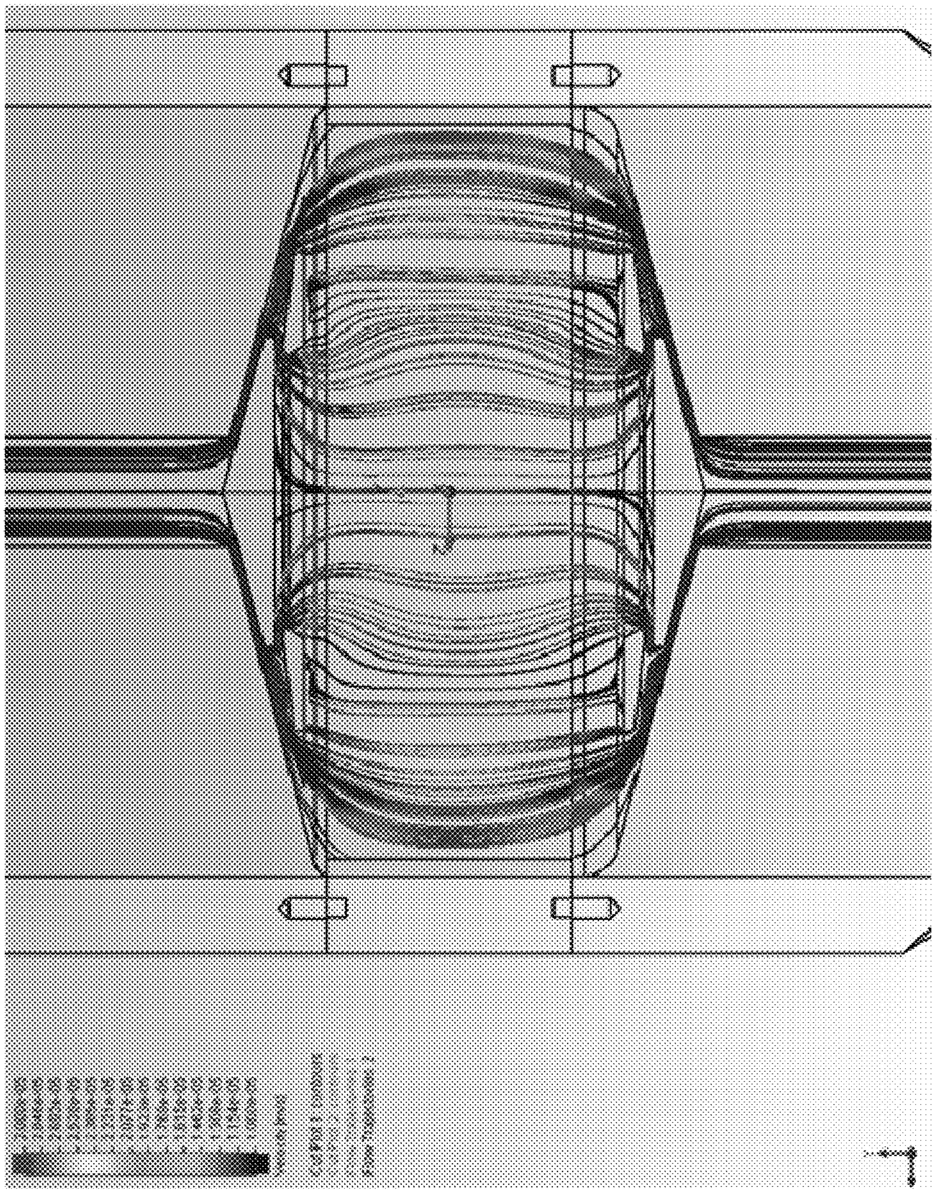
FIG. 9 illustrates a flow rate profile through the 3D bioreactor when using the fluid distributor.

It should next be noted that the fluid distributor 22 (FIG. 8) is preferably such that it will improve the flow uniformity through the 3D bioreactor. The design of the inlet, outlet, and fluid distributor also preferably takes into consideration the following: (1) improve the flow uniformity through the 3D bioreactor; (2) minimization of the dead-volume 24 at inlet and outlet to reduce the overall priming volume of the bioreactor; and (3) preventing bubble collection inside the bioreactor. FIG. 9 shows the flow velocity profile throughout the 3D bioreactor based on CFD simulation by using the fluid distributor. The use of the fluid distributor (FIG. 8) improved the uniformity of the flow. The maximum flow rate (around 30 μm/s) and the minimum flow rate (around 10 μm/s) are relatively close to each other and serve to promote uniform laminar flow (i.e. flow of fluid in relatively parallel layers). A relatively uniform flow rate everywhere in the bioreactor will also provide smaller differences of shear stress to cells residing at different locations in the bioreactor.

The 3D bioreactor can be fabricated by other additive manufacturing technologies such as selective laser sintering (SLS), stereolithography (SLA), Digital Light Processing (DLP), and etc. FIGS. 7*b*, 7*e*, 7*f*.

For the 3D printed bioreactor (FIG. 7*d*) using ABS, the hydrophobic internal surfaces of the bioreactor is preferably modified to allow for cell adherence. Polydopamine as a primer coating followed with fibronectin coating was therefore utilized to improve the ABS surfaces. To optimize the coating procedure, coating using different concentrations of dopamine hydrochloride (Sigma #H8502) and fibronectin (Sigma #F1141) was evaluated on the substrates of both medical grade and non-medical grade ABS, respectively. Incubation of the ABS surface in a 0.25 mg/mL dopamine dissolved in 10 mM Tris buffer (pH=8.5 at 25° C.) for a period of about 18 hours, resulted in an effective polydopamine layer for the subsequent fibronectin coating. After the polydopamine coating, a four-hour incubation of the ABS surface in fibronectin (Fibronectin from bovine plasma), with the concentration of 50 or 100 μg/mL, promoted mesenchymal stem cell attachment. It should be noted that the use of the polydopamine plus the fibronectin coating is contemplated for use on bioreactors other than the ABS based 3D bioreactor disclosed herein, and in particular on bioreactors that are fabricated with hydrophobic materials. It should also be noted, that the polydopamine primer coating can be combined with other coatings such as peptides, collagen, laminin, multiple cell extracellular matrix proteins, or selected antibodies that are required by particular cell types. After polydopamine is deposited on the bioreactor surface, it can then bind with functional ligands via Michael addition and/or Schiff base reactions. The ligand molecules therefore include nucleophilic functional groups, such as amine and thiol functional groups.

Figure 10A:
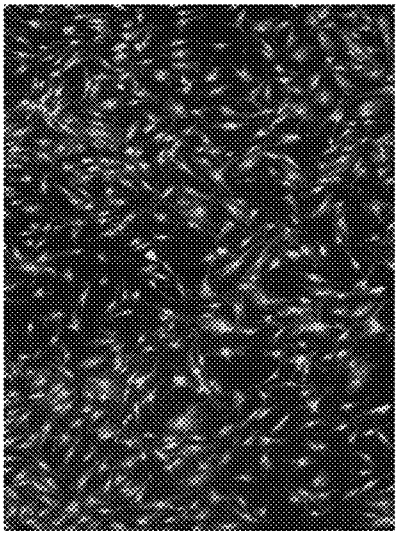
FIGS. 10*a*, 10*b* and 10*c* show cell attachment on a substrate made of non-medical grade ABS resin with polydopamine and fibronectin coating.
Figure 10B:
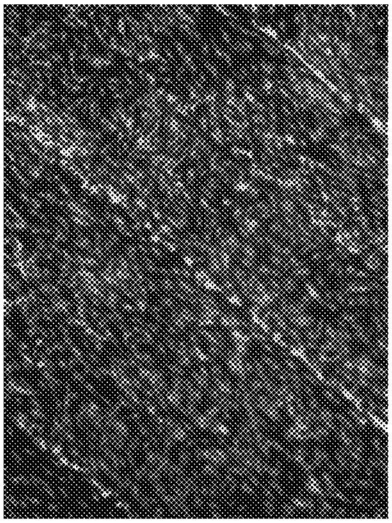
Figure 10C:
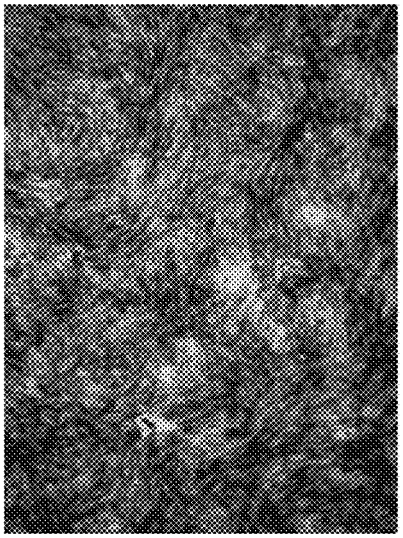
Figure 10D:
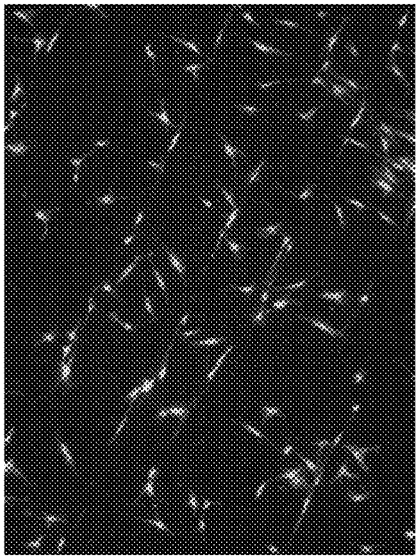
FIGS. 10*d*, 10*e* and 10*f* show cell attachment on a substrate made of medical grade ABS resin with polydopamine and fibronectin coating.
Figure 10E:
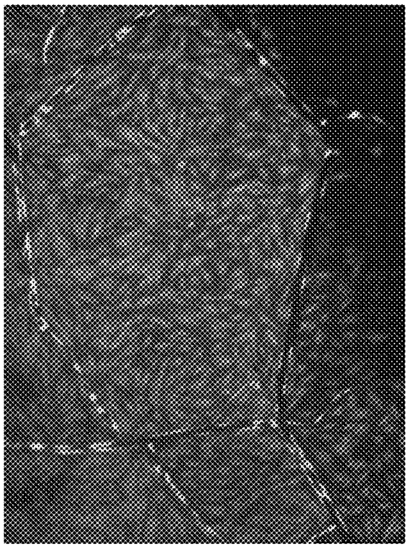
Figure 10F:
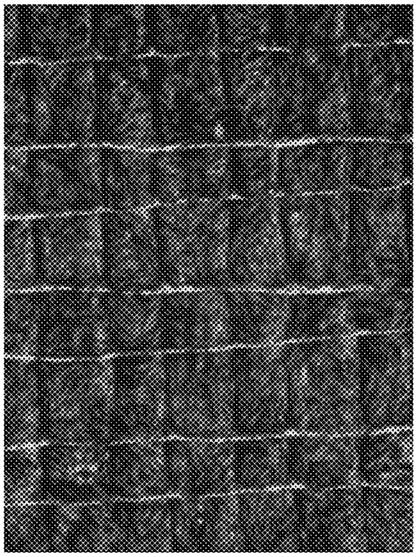

FIGS. 10*a*, 10*b* and 10*c* show cell (labeled with green fluorescence) attachment on non-medical grade ABS at concentrations for coating at 20 μg/ml fibronectin, 50 μg/ml fibronectin and 100 μg/ml fibronectin, respectively, after the polydopamine coating described above. FIGS. 10*d*, 10*e*, and 10*f* show cell attachment on the medical grade ABS at concentrations for coating of 20 μg/ml fibronectin, 50 μg/ml fibronectin and 100 μg/ml fibronectin, respectively. These figures suggest that both medical and non-medical grade ABS have similar performance in cell attachment after polydopamine/fibronectin coating. The coating of fibronectin at 50 μg/ml or 100 μg/ml concentration are preferred for a good cell attachment. These figures also show that cells were aligned to the surface texture that was generated during the 3D printing process. Therefore, a bioreactor surface generated by SLA or DLP 3D printing is preferred for cell expansion.

Figure 11B:
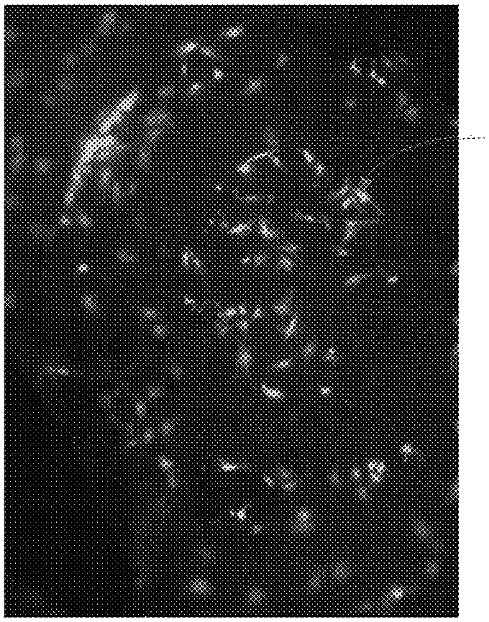
FIGS. 11*a*, 11*b* and 11*c* illustrate cell attachment onto the 3D bioreactor surface.
Figure 11C:
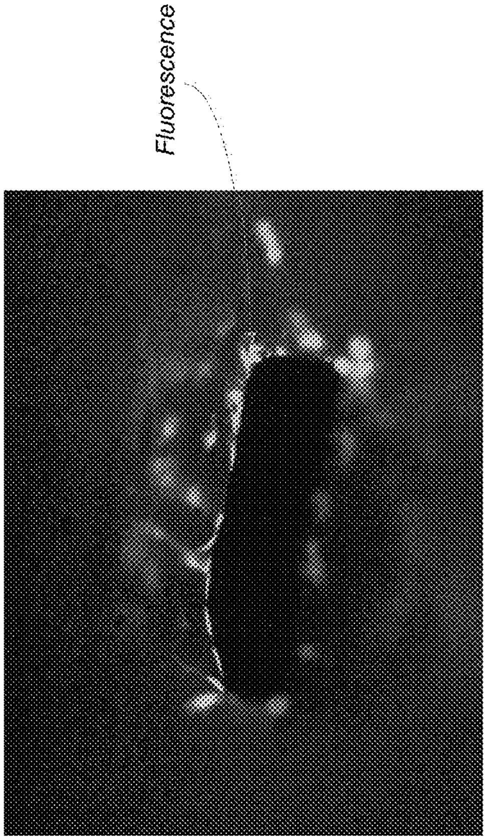
Figure 11A:
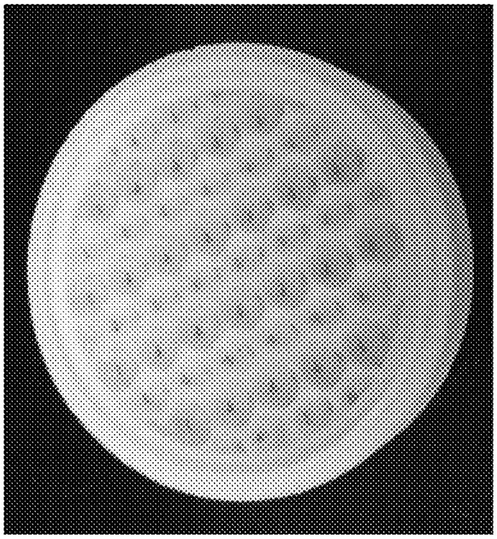

Cell attachment was also evaluated on the 3D bioreactor. Reference is made to FIGS. 11*a*, 11*b* and 11*e*, which illustrate that the cells (labeled with green fluorescence) attach well onto the 3D bioreactor surface. FIG. 11*a* shows the 3D bioreactor fixed-bed, FIG. 11*b* shows cells (labeled an arrow pointing to the green fluorescence) seeded on the surface of the spherical voids and FIG. 11*e* shows cells reside near an interconnected pore between the spherical voids.

As alluded to above (FIG. 3) the 3D bioreactor herein is preferably utilized in a perfusion system. More specifically, a 3D bioreactor fixture was placed inside a 37° C. incubator to maintain the system at body temperature. A Cole-Parmer Masterflex pump was used to deliver cell culture medium to the bioreactor after passing through an oxygenator. A MCQ 3-channel gas blender mixed proper amounts of oxygen, carbon dioxide, and nitrogen to provide a gas mixture feeding to the oxygenator to condition the cell culture medium. With the gas blender, the gas mixture can be controlled to produce a hypoxic condition with around 2% oxygen concentration if needed, which is contemplated to provide relatively more rapid growth of mesenchymal stem cells than at oxygen concentrations of 21%. A gas blender can also adjust the oxygen concentration accordingly with the increase of total cell numbers in the bioreactor. In addition, in the perfusion system, the 3D bioreactor during cell seeding can be preferably positioned horizontally and connected to a stepper motor so that the bioreactor rotates around the bioreactor axis so that the cells are more uniformly seeded inside the bioreactor.

Cell seeding of the 3D bioreactor may be achieved as an example as follows. For the 3D bioreactor illustrated in FIGS. 7*a*-7*d*, the total priming volume of the bioreactor is about 22 mL, which includes the volume of the fixed-bed (~16 mL) as well as the space of inlet and outlet (~6 mL). A total of $1.5\times10^6$ mesenchymal stem cells, suspended in 25 mL, were infused into the bioreactor. The infusion was carried out by a syringe pump using an infusion rate of 2 mL/min. Right after medium infusion, the bioreactor was placed horizontally on the bioreactor fixture to allow the bioreactor to slowly rotate around its axis with a rotation rate of 0.15 RPM. The bioreactors herein may therefore be rotated at a rotation rate in the range of 0.5 RPM to 0.5 RPM. The bioreactor was allowed to rotate for about 6 hours followed by start of the perfusion flow. A high loading efficiency of 96.3% was measured using this cell loading method.

To observe the cell distribution inside bioreactor after seeding, the cells were fixed on the surface of the bioreactor. The fixed cells were then stained with DAPI fluorescence dye (blue) to label the cell nuclear. Then the bioreactor was spliced to open the internal chamber and fluorescence microscopy was used to view the cell attachment and distribution on different surfaces inside the bioreactor. FIGS. 12*a*, 12*c*, 12*e*, and 12*g* illustrate the cell distribution on the inlet, fixed-bed, wall, and fluid distributor, respectively. All areas indicated seeded cells with a relatively low cell density. The images indicate that the cell seeding was relatively uniformly distributed throughout the bioreactor.

Figure 12A:
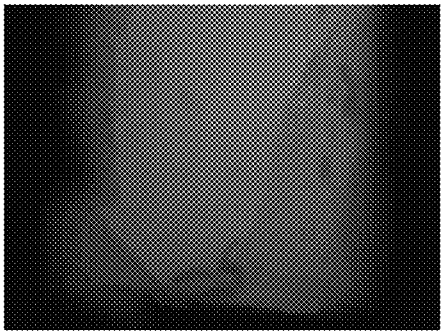
FIGS. 12*a*, 12*c*, 12*e* and 12*g* illustrate cell attachment on the inlet, fixed-bed, wall and fluid distributor of a 3D bioreactor after cell seeding.
Figure 12B:
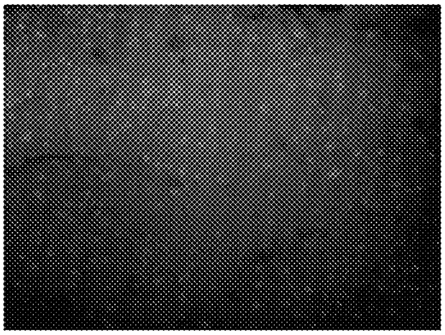
FIGS. 12*b*, 12*d*, 12*f* and 12*h* illustrate cell distribution after a 7-day culture period.
Figure 12C:
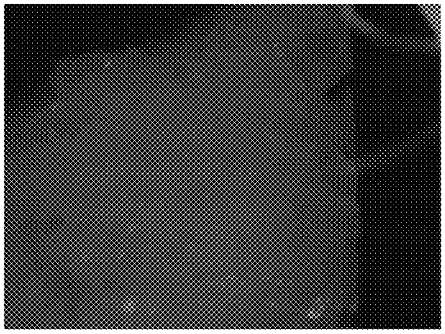
Figure 12D:
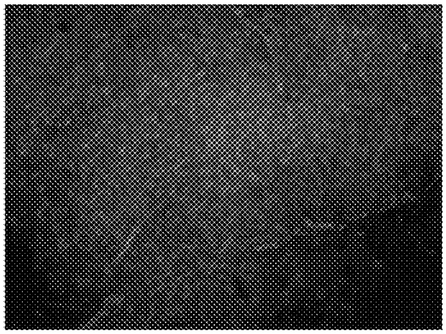
Figure 12E:
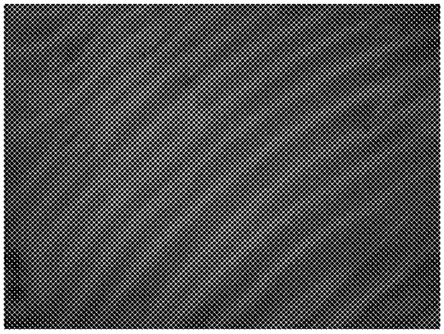
Figure 12F:
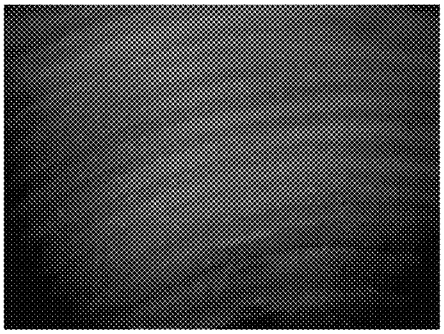
Figure 12G:
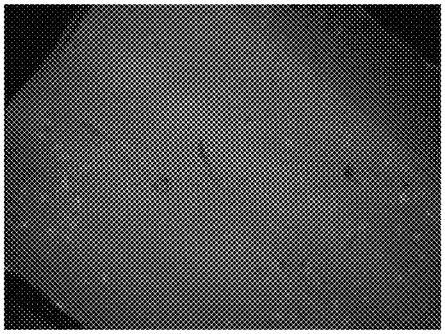
Figure 12H:
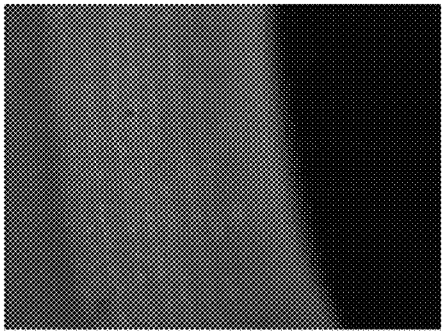

FIGS. 12*b*, 12*d*, 12*f*, and 12*h* indicate the cell distribution on the corresponding surfaces inside the bioreactor after a 7-day expansion period. FIGS. 12*a* and 12*b* are the 3D bioreactor inlet wall, FIGS. 12*c* and 12*d* are on the 3D bioreactor inner wall, FIGS. 12*e* and 12*f* are on the 3D bioreactor center-void spherical surface, and FIGS. 12*g* and 12*h* are on the 3D bioreactor flow guider surface.

After a static (no medium perfusion) cell seeding period, the 3D bioreactor is preferably placed in vertical position (the bioreactor inlet is lower than the outlet) during perfusion to prevent the collection of air bubbles inside the bioreactor. The assembled bioreactor shown in FIG. 7*d* was perfused at the flow rate of 2 mL/min. According to the CFD simulation, the laminar flow rate of 38.5 μm/sec will not generate relatively high shear stress to cells. For this bioreactor shown in FIG. 7 with the fixed-bed diameter of 4.28 cm, or about 14.4 $cm^2$ of cross-sectional area the calculated equivalent flow rate is 3.3 mL/min. It should be noted volume perfusion rate depends on the total volume and the cross-sectional area of the bioreactor, the spherical voids diameter and pore diameters inside the bioreactors, as well as cell types, oxygen and nutrition consumption, shear tolerance, etc. Therefore, an optimized perfusion rate will need to be determined via cell manufacturing process development.

The cell culture medium circulated through an oxygenator before flowing into the 3D bioreactor. A gas blender produced a gas mixture containing 74% of $N_2$, 21% of $O_2$, and 5% $CO_2$, which was fed into the oxygenator to refresh the cell culture medium before delivery to the cells inside the bioreactor.

Figure 13A:
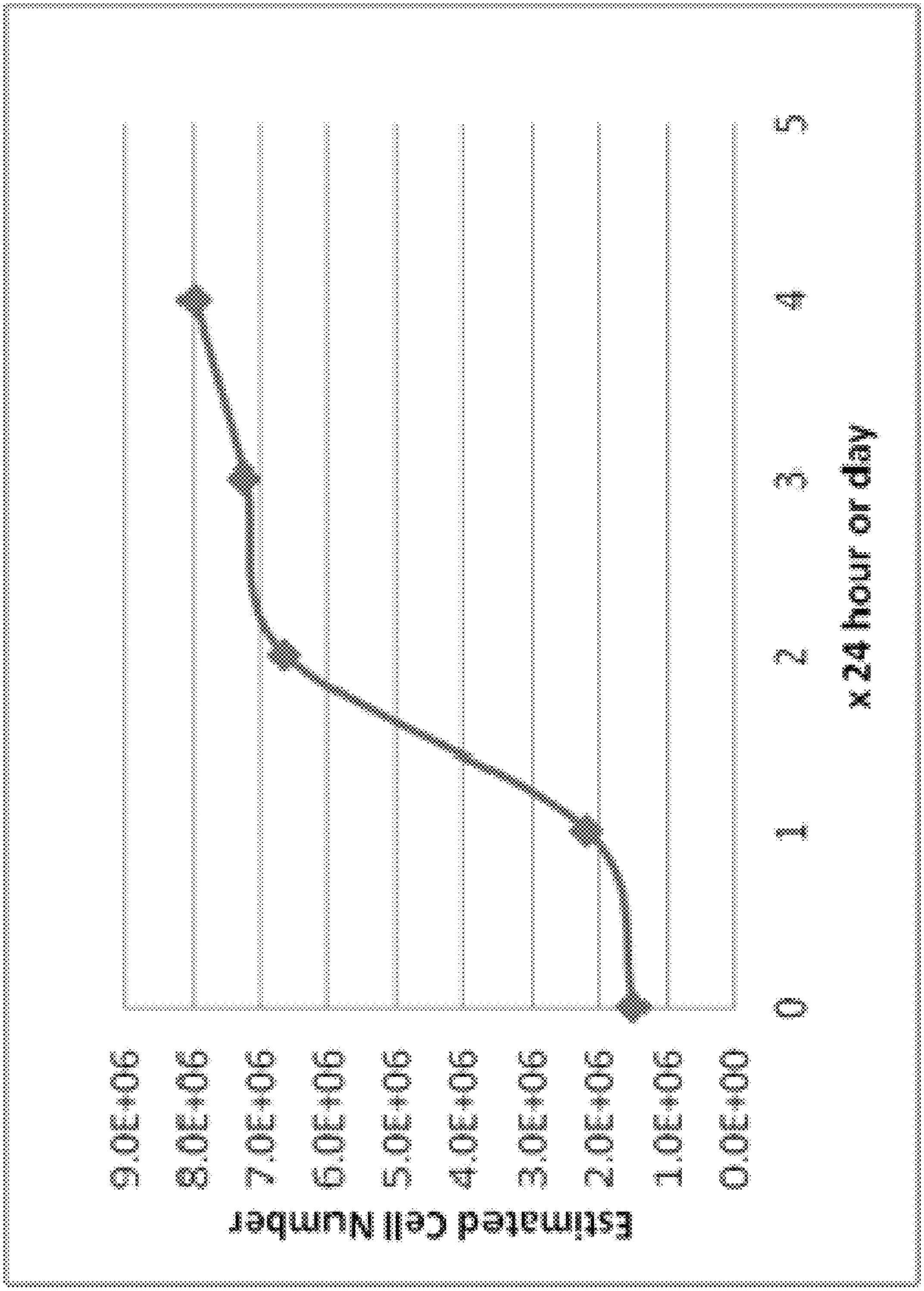
FIG. 13A illustrates the change in cell numbers in the 3D bioreactor over a four-day period.

Every 24-hour, the change in glucose and lactate was measured. Based on glucose and lactate change, the number of cells inside the bioreactor was estimated. FIG. 13A illustrates the change of cell number in the bioreactor over a four-day period. The growth curve shows the three periods of cell growth: that is, slow cell growth (day 1), exponential cell growth (day 2), and growth plateau (days 3 and 4). Around $8\times10^6$ cells at harvest are expected after 4-day expansion.

Figure 13B:
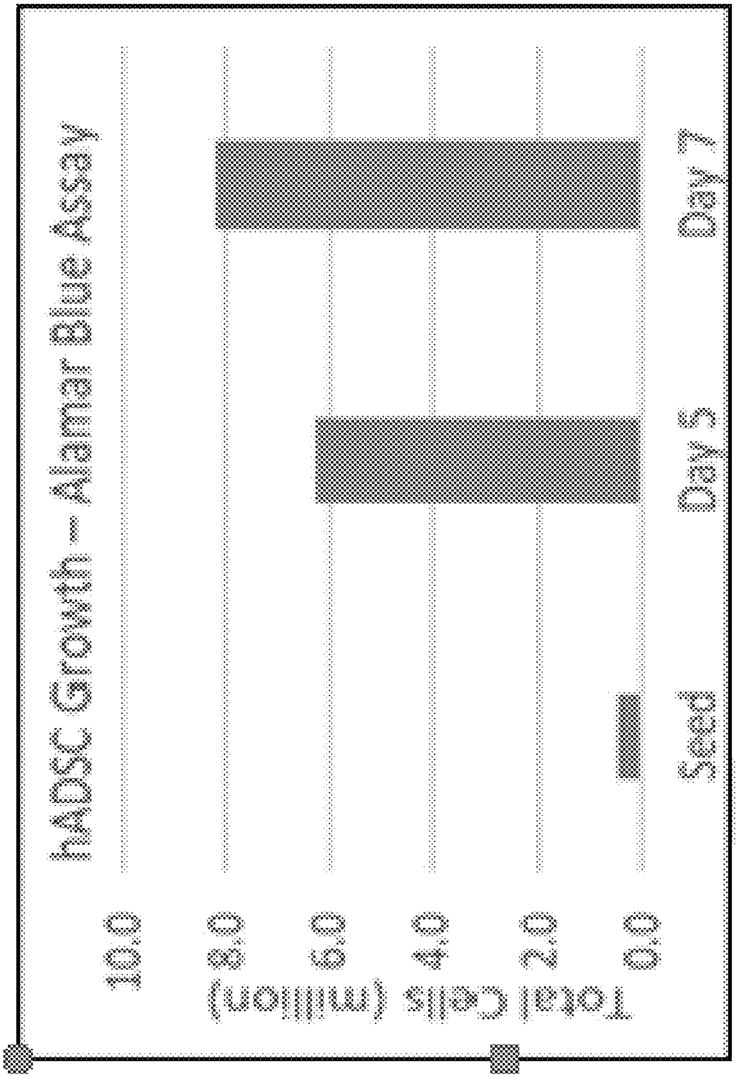
FIG. 13B illustrates the expansion of human adipose stem cells using the 3D bioreactor herein.
Figure 13C:
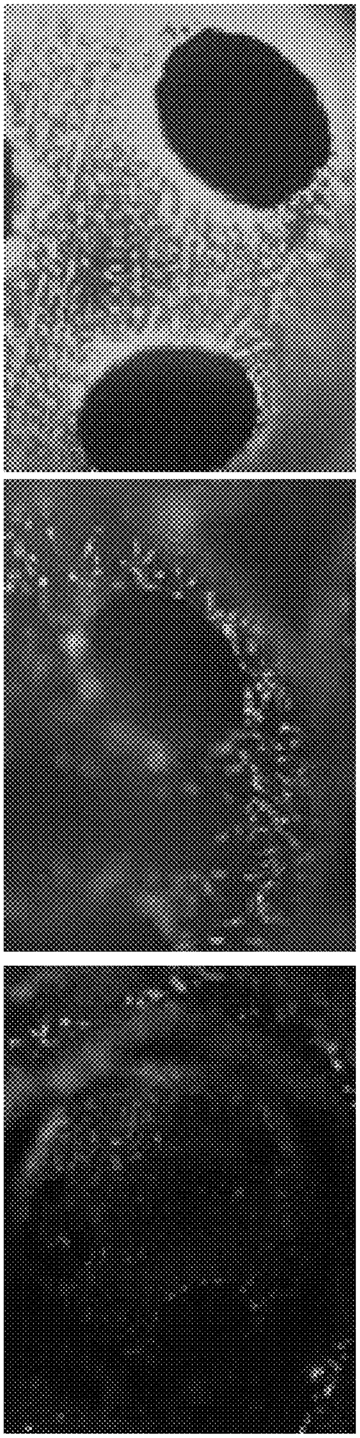
FIG. 13C illustrates the green fluorescence images showing live cells human adipose stem cells growing on the internal surfaces of the 3D bioreactor.

FIG. 13B next illustrates the expansion of human adipose stem cells (hADSC) using the 3D bioreactor herein. The cell growth is illustrated by the cell number estimated from Alamar Blue Assay. FIG. 13C provides the green fluorescence images showing live cells growing on the internal surfaces of the 3D bioreactor.

Figure 14:
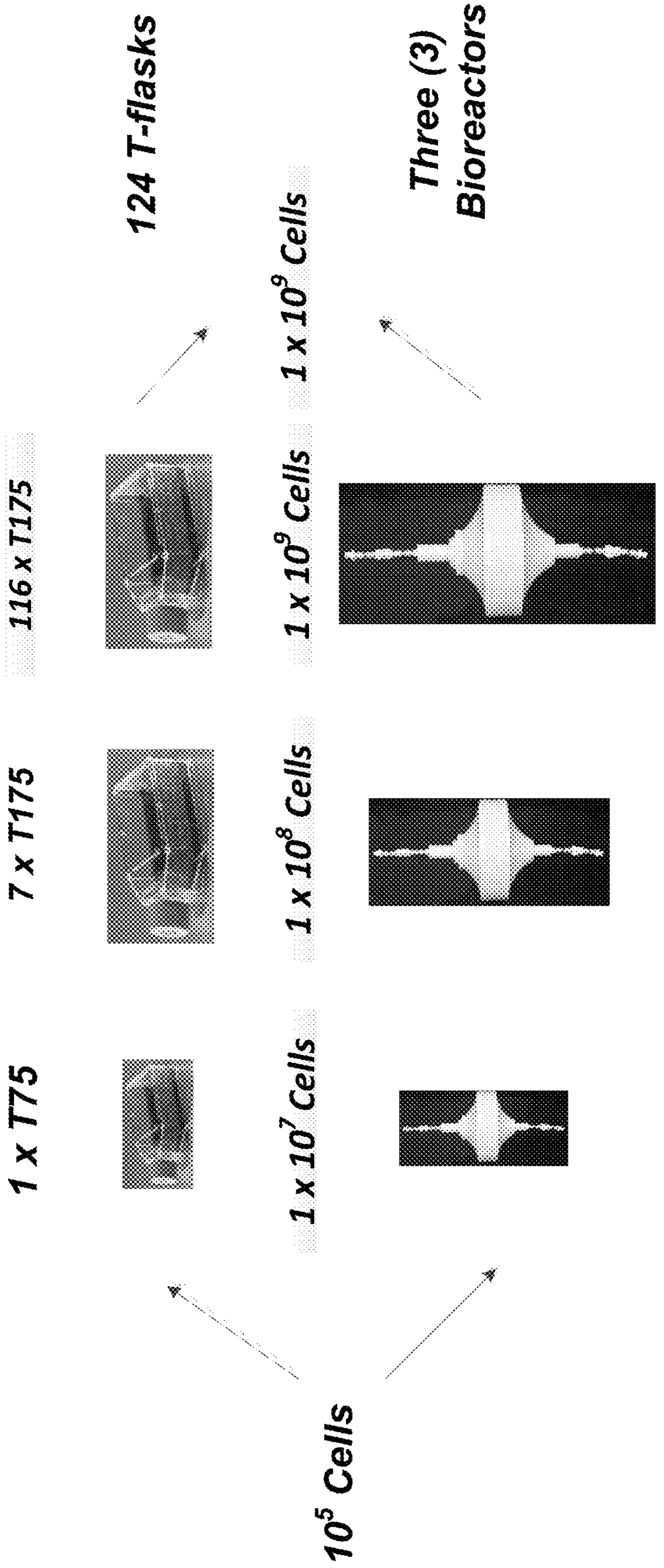
FIG. 14 illustrates a comparison of the use of the 3D bioreactor herein, of three different sizes, versus the use of over 120 T-flasks, to provide the indicated level of cell expansion.
Figure 15A:
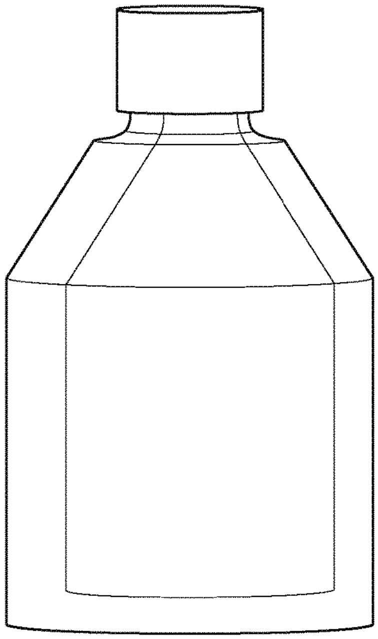
FIG. 15*a* illustrates a T 25 culture flask.
Figure 15B:
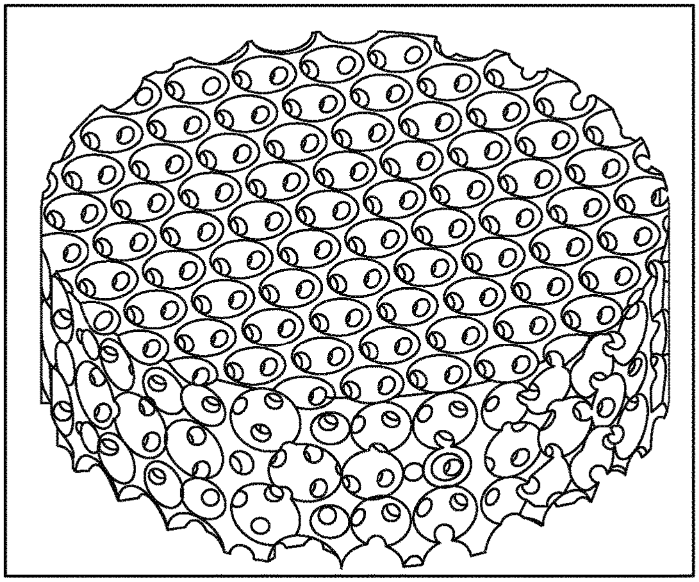
FIG. 15*b* illustrates a 3D bioreactor scaffold.
Figure 15C:
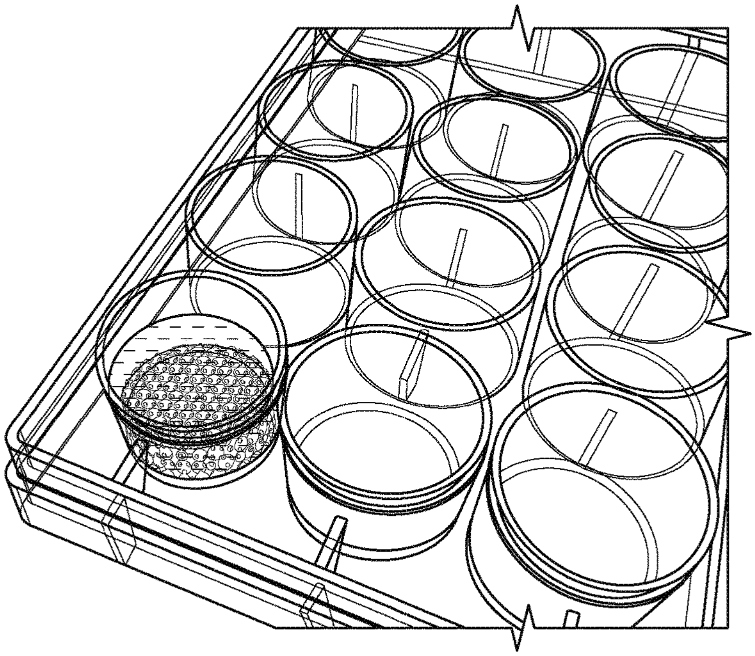
FIG. 15*c* illustrates the 3D bioreactor placed in a cell culture medium after seeding.

Assuming cells are harvested at 80% of confluence or about $0.4\times10^5$ cells/$cm^2$, the bioreactors that have the $10^7$, $10^8$, and $10^9$ cell expansion capacity as shown in FIG. 14 would require a total cell culture surface area of 250 $cm^2$, 2,500 $cm^2$, and 25,000 $cm^2$, respectively. Assume the bioreactor is comprised of 2.0 mm diameter spherical voids and twelve (12) 0.5 mm diameter interconnected pores. Each spherical void has SAu=10.16 $mm^2$. In other words, the bioreactor that has a $10^7$, $10^8$, and $10^9$ cell expansion capacity requires 2,461, 24,606, and 246,063 of 2.0 mm spherical voids. Considering each spherical void has the volume of 4.19 $mm^3$, a reasonable packing efficiency of 73.6% (according to SolidWorks™ computer simulation), the bioreactor that has a $10^7$, $10^8$, and $10^9$ cell expansion capacity requires a volume of 14.0 $cm^3$, 140.1 $cm^3$, and 1400.8 $cm^3$, respectively. Packing efficiency is reference to the volume occupied by the spherical voids ($V_{occupied}$) divided by the total volume of a 3D cylinder space ($V_{cylinder}$) having a given diameter Φ and height H. For the 3D bioreactor herein, packing efficiency preferably has a value of greater than 64.0%, more preferably greater than 70.0% and most preferably a value greater than 75.0%. Assume the bioreactor's diameter Φ and height H have the ratio of 3:1, then the bioreactors with the $10^7$, $10^8$, and $10^9$ cell expansion capacities shown in FIG. 15 have Φ and H of 5.2 cm (Φ) and 1.7 cm (H), 16.4 cm (Φ) and 5.5 cm (H), 51.8 cm (Φ) and 17.3 cm (H), respectively. The bioreactor is also expected to be scalable to $10^{10}$, $10^{11}$, $10^{12}$ cell expansion capacity.

Cell detachment from the 3D bioreactor was then evaluated. Two reagents were tested for cell detachment. One was the traditional Trypsin-EDTA (0.25%), the other was the new TrypLE Select. The latter is expected to be a superior replacement for Trypsin. Using Trypsin with about 5-minute of warm (37° C.) incubation period, it was possible to successfully detach >95% of cells from the 3D bioreactor.

Viral Vector Production

As noted above, the 3D bioreactor herein has been found particularly suitable for the expansion of adherent viral vector producing cells and the ensuing harvest of viral vectors. Adherent viral vector producing cells is a reference to the feature that the cells attach to the 3D bioreactor surface. The 3D bioreactor as described herein is preferably treated so that as alluded to above, the surface is made hydrophilic so that the preferred viral vector producing cells, HEK 293T cells, can attached and grow on the 3D bioreactor surface.

Preferably, surface treatments include UV/ozone treatment, plasma treatment, and coating of the bioreactor surface with extracellular matrix proteins such as fibronectin, collagen, laminin, gelatin, and etc. A comparison was conducted for cell attachment with three different UV/ozone treatment conditions. The inlet of a scaffold input with ozone and the outlet released the ozone to an oil bath inside a flammable hood. The air flow to the ozone generator was set at 2 mL/min. During ozone treatment, the bioreactor was exposed to a UV 254 nm light. The UV/ozone treatments were for 3 min, 5 min, and 10 min. The 3D bioreactor with different lengths of ozone treatment were then compared for their capability for HEK 293T cell attachment.

A total $5\times10^5$ HEK 293T cells, suspended in 1.75 mL of oxygen-balanced cell culture medium, were filled inside each of three bioreactors with different lengths of UV/Ozone treatment. The cells were incubated in the bioreactor for four hours while the bioreactor was rotating axially at 0.15 RPM. After 4 hours, non-attached cells were flushed out from the bioreactor. Table 2 illustrates the HEK 293T cell attachment under different lengths of UV/ozone treatment. The results indicate that the bioreactor with 10 minutes UV/Ozone treatment had the most cell attachment. This result is also confirmed in the later described experiments where the HEK 293T cells were cultured on the 3D bioreactor scaffolds without an inlet and outlet as discussed below.

TABLE 2

HEK 293T Cell Attachment and UV/Ozone Treatment of 3D Bioreactor

| UV/Ozone Treatment | Seeding Cells | Non-Attached Cells | % Cell Loss |
|---|---|---|---|
| 3 min | $5\times10^5$ | $1.13\times10^5$ | 22.5% |
| 5 min | $5\times10^5$ | $8.75\times10^4$ | 17.5% |
| 10 min | $5\times10^5$ | $5.00\times10^4$ | 10.0% |

Comparison of Viral Vector Production Between Traditional T-flasks and 3D Bioreactor Scaffolds Before the experiments using the perfusion-based 3D bioreactor described herein, an initial test was conducted utilizing the 3D bioreactor scaffolds herein under a static cell culture condition (i.e., without an inlet or outlet as in the perfusion procedure). Under these conditions, one can image the HEK 293T cells attachment and growth on the internal surface of the 3D bioreactor scaffolds, to confirm the growth of HEK 293T cell within the bioreactor.

An exemplary process flow diagram of GFP (green fluorescence protein) lentiviral vector production is now shown in Table 3. HEK 293T cell lines (ATCC #CRL-11268) were used as the packaging cell. The HEK 293T cells were cultured in high-glucose DMEM culture media with 2 mM L-Glutamine and 10% heat-inactivated fetal bovine serum (FBS). A third-generation Lentiviral Packaging plasmids (Origene, Cat #TR30037) and Lenti vector with C-terminal GFP tag (Origene, Cat #PS100065) were purchased and used in this study for lentiviral vector production. The use of this transfection mixture or reagent to transfect HEK 293T cells is contemplated to produce GFP lentiviral vectors. In addition, it should be noted that a transfection reagent herein is reference to a reagent that will either enhance or inhibit a specific gene expression in the cell. The transfected cells will express the GFP themselves and at the same time produce more GFP lentiviral vectors. The produced GFP lentiviral vectors are then capable to deliver the GFP genes into other target cells via transduction. Transduction is reference to the delivery of genetic material to target cells. Successfully transduced target cells will express GFP and thus convert the originally transparent cells to cells emitting green fluorescence in the current and following generations. Cells expressing GFP in this case are then easily imaged under a fluorescence microscope.

TABLE 3

Flow Diagram of Lentiviral Vector Production

| Day 1: Seeding HEK 293 cells at density $3 \times 10^4$ cells/cm$^2$ | Day 2: Deliver the transfection medium to cells with TurboFectin transfection reagent | Days 4 & 5: Collect 2 batches of viral vectors from the cell culture media | Day 5: Storage the viral vector at 4° C. for couple days or freeze the viral vector at −80° C. | >Day 6: Characterize viral vectors |
|---|---|---|---|---|

In this study, the lentiviral vector upstream production efficiency was compared between T-25 flasks and the 3D bioreactor scaffolds herein that both have the same cell culture surface area of 25 cm$^2$. See FIG. 15*a*, T-25 culture flask, FIG. 15*b*, 3D bioreactor scaffold, and FIG. 15*c*, the 3D bioreactor scaffold placed in the cell culture medium after seeding. In order to compare the functional efficacy of the viral vectors produced by the 3D bioreactor herein and the standard culture flask, lentiviral vectors were employed that carried a transfer vector coded GFP as described above. The efficacy of cell transfection and transduction were assessed by the green fluorescence intensity imaged from the transfected or transduced cells. The yield of the lentiviral vectors was estimated using a real time PCR assay.

A total $5 \times 10^5$ HEK-293T cells, suspended in 1 mL of cell culture medium, were seeded on the 3D bioreactor placed in a six-well plate with ultra-low attachment surface. The six-well plate with ultra-low attachment surface was used to ensure all cells were attached on the 3D bioreactor instead of on the bottom of the six-well plate. A silicone gasket was placed in the well to allow the scaffold seated in the center of the gasket to prevent the cell culture medium from leaking out of the 3D bioreactor scaffold so that most of the seeding cells attached to the scaffold. After overnight cell seeding, the scaffold was moved to a new twelve-well plate with ultra-low attachment surface (FIG. 15*c*) for expansion. Eighteen hours after seeding, the medium containing antibiotics were replaced by an antibiotics-free medium. Four hours later, or twenty-four hours after seeding, the HEK 293T cells were transfected with lentiviral vector plasmids with GFP. The transfection medium was removed and replaced by fresh antibiotic-free medium eighteen hours after transfection. The transfected cells were visualized with fluorescence microscopy because the cells started to show green fluorescence.

Figure 16:
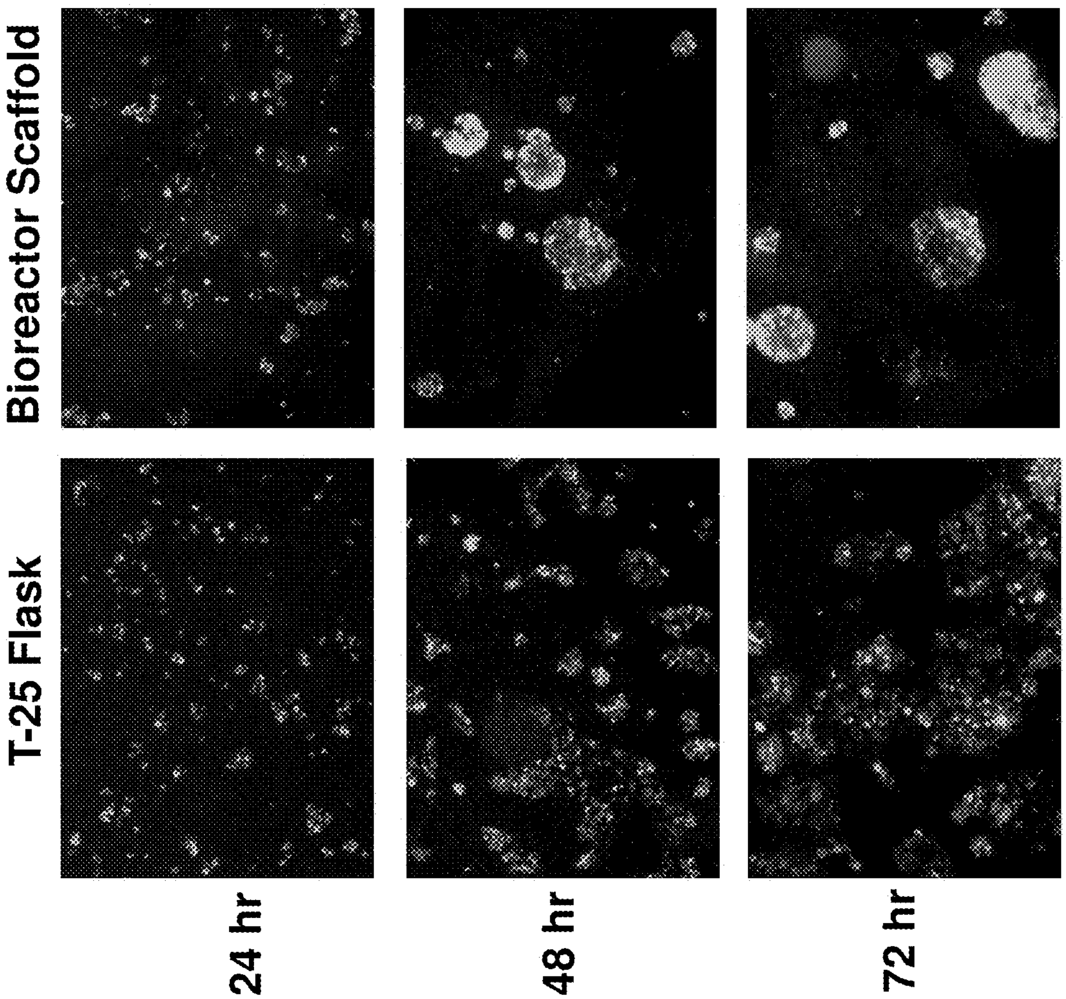
FIG. 16 illustrates the green fluorescent images of the transfected HEK-293T cells on the T-25 flasks and the 3D bioreactor scaffold at 24, 48, and 72 hours after the transfection.

FIG. 16 illustrates the green fluorescent images of the transfected HEK-293T cells on the T-25 flasks and the 3D bioreactor scaffold at 24, 48, and 72 hours after the transfection. The images indicate that the cells cultured on both substrates were transfected successfully. The cell culture mediums were collected 24 and 48 hours after transfection and the yields of the GFP lentiviral vector were quantified using the Applied Biosystems' real time PCR instrument. Table 4 compares the yields of the GFP lentiviral vector from the cells cultured on the T-flask and the 3D bioreactor scaffold. The result indicates that the lentiviral vector from cells cultured on the bioreactor scaffold is more than twice the amount as that from the cells cultured on the T-25 flask when same number of cells were cultured on the same surface areas. The higher yield from the cells cultured on the bioreactor scaffold is believed due to the cells residing on the 3D space inside the scaffold having a relatively higher transfection efficiency.

TABLE 4

Yield Comparison of GFP Lenticular Vectors

| Supernatant Collected | T-25 Flask | 3D Bioreactor Scaffold |
|---|---|---|
| Volume (48 & 72 hr) | 6 mL | 2 mL |
| 48 hr Lentiviral Concentration (TU/mL) | $7.9 \times 10^5$ | $3.7 \times 10^6$ |
| 72 hr Lentiviral Concentration | $4.6 \times 10^5$ | $5.3 \times 10^6$ |
| Total Collected Viral Particles | $7.5 \times 10^6$ | $1.8 \times 10^7$ |

Validate the Function of the Viral Vectors Produced by 3D Bioreactor Scaffolds This experiment was to show that the viral vector produced from the HEK 293T cells cultured on the 3D bioreactor scaffold can transduce other target cells at the same multiplicity of infection (MOI) as a commercially available GFP viral vector pLenti-C-mGFP (Origene, Cat #PS100071V). Before the experiment, the viral titer (concentrations) for the produced GFP viral vector and the purchased pLenti-C-mGFP were determined to be $5.31\times10^6$ and $3.31\times10^8$ TU/ml, respectively, by real time PCR.

Both GFP vectors were used to transduce a new batch of HEK 293T cells that were not involved in producing the GFP lentiviral vectors. A 96 well plate was used for seeding the cells at a seeding density of 240,000 cells/$cm^2$, which amounts to 76,800 cells per well. The plate was coated with 0.2% gelatin to ensure proper attachment of the HEK 293T cells. After overnight incubation of the seeded cells, the cells were transduced before they could double in 20 hours. The MOIs used for the experiment were 1, 3, 5, and 10, respectively. A 0.2 μl cationic polymer polybrene was used per well to enhance the transduction efficiency.

Figure 17:
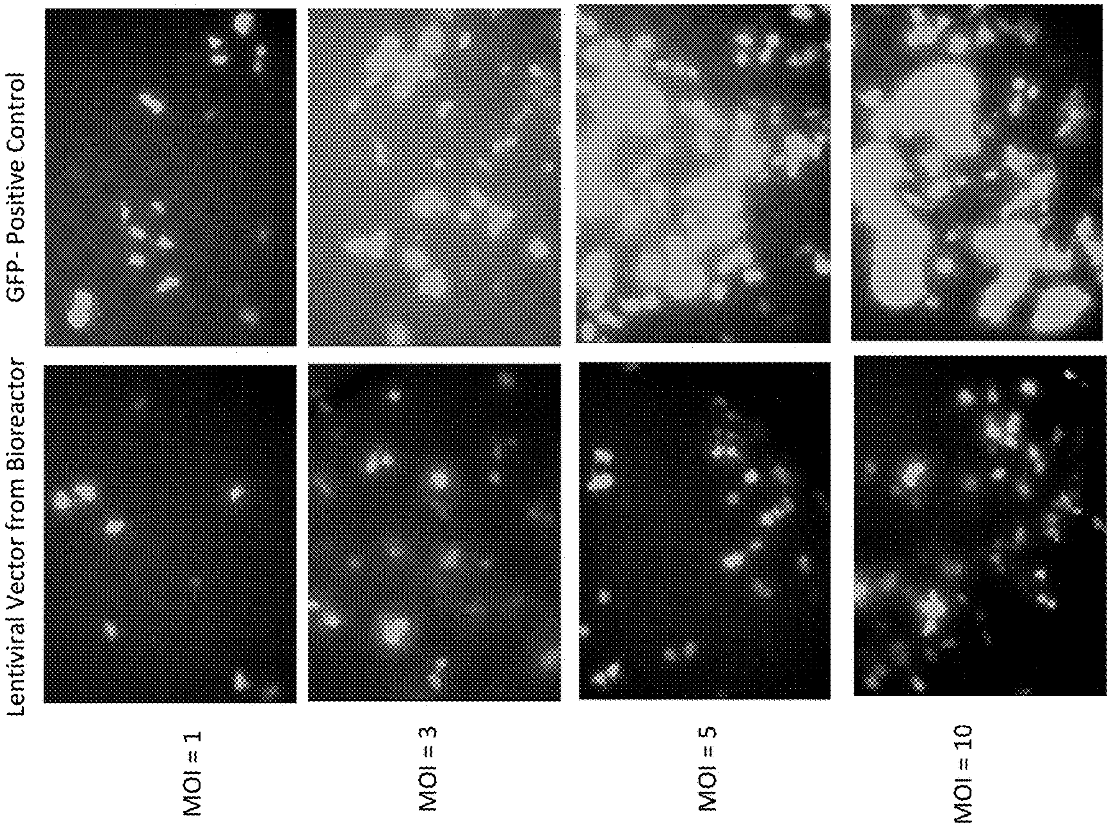
FIG. 17 illustrates the FITC fluorescent images (20× objective lens) and compares transduction of HEK 293T cells using GFP viral vector produced form cells seeded on the 3D bioreactor scaffold (left column) and commercially available pLenti-C-mGFP viral vector.

The results are illustrated in FIG. 17, which indicates that the GFP viral vectors produced by the 3D bioreactor scaffold can transduce HEK 293T cells at the same MOIs as the commercially available pLenti-C-mGFP viral vector. This study shows the efficacy of the 3D bioreactor scaffolds herein for lentiviral vector production.

Viral Vector Production Using a Perfusion-Based 3D Bioreactor

Figure 18:
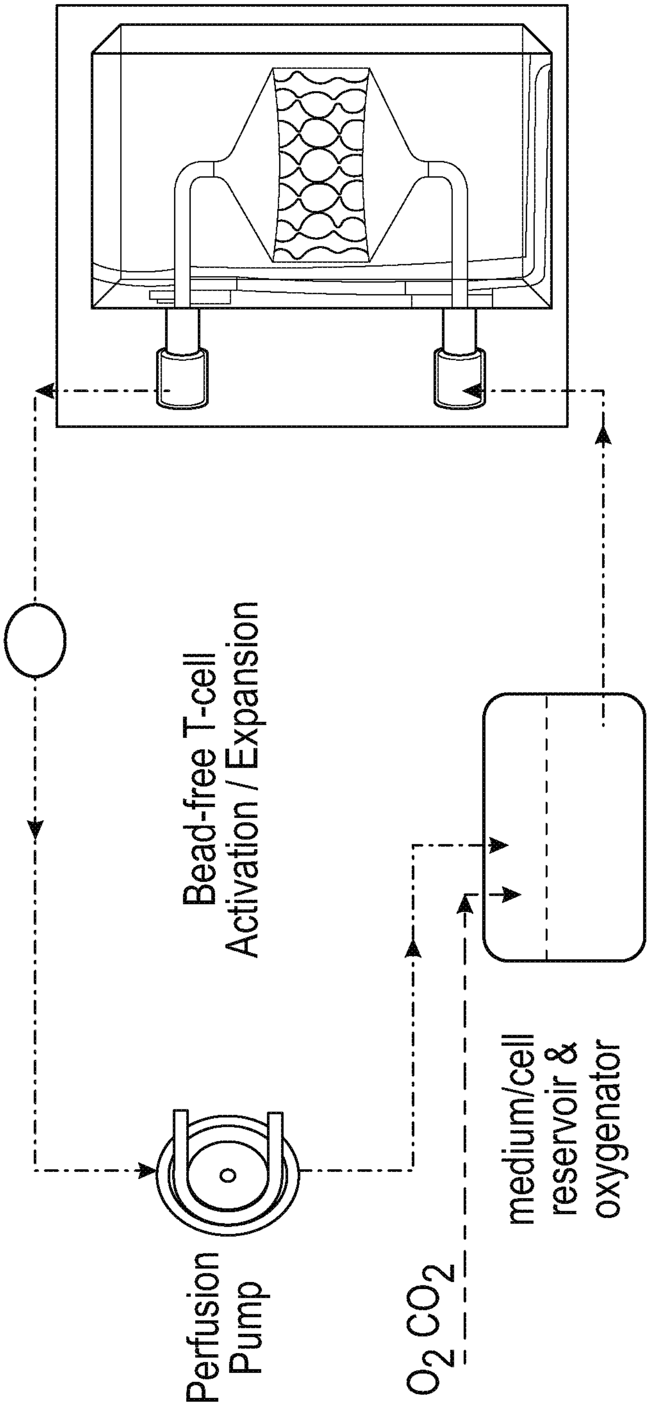
FIG. 18 illustrates a perfusion based 3D bioreactor for viral vector production.

To demonstrate the automated viral vector production, a perfusion-based bioreactor cell culture (FIG. 18) was configured. In this study, HEK 293T cells were cultured in the 3D bioreactor that has a matrix dimension of 14.4 mm×6.25 mm (diameter×height) and a total internal surface area of 24.1 $cm^2$. The bioreactor is made of interconnected spherical voids of 3 mm diameter with the interconnected pore diameter of 0.5 mm. Cell culture media flows into the inlet of the bioreactor and out from the outlet of the bioreactor driven by a peristaltic pump. This 3D bioreactor used in this study can be readily scaled up to bioreactors with relatively larger dimensions while the internal cell culture structure remains the same.

Based upon the above, a perfusion-based bioreactor was set-up for viral vector production. A total of $5\times10^5$ HEK-293T cells, suspended in 1.75 mL cell culture medium, were filled in the bioreactor. Then the inlet and outlet of the bioreactor were closed and the bioreactor was held for axial rotation) for 4 hours to seed the cells on the internal surface of the bioreactor. After the seeding, the bioreactor was connected into the perfusion system and the medium was perfused through the bioreactor at a rate of 0.5 mL/min.

Eighteen hours after seeding, all the medium was empty from the bioreactor and reservoir and replaced by an antibiotic-free medium. Four hours later, a 2-mL transfection medium was prepared with antibiotic-free, oxygen-balanced medium. Then the bioreactor was filled with 2 mL of the transfection medium driven by the pump at 0.5 mL/min. The pump stopped when the bioreactor was filled. The transfection medium was incubated inside the bioreactor statically for six hours. Then the transfection medium was withdrawn from the bioreactor and perfusion circuits, replaced by the original antibiotic-free medium. The first viral vector collection occurred at 24 hours after transfection. During collection, all medium in the circuits was collected and the perfusion circuit was replaced with fresh antibiotic-free medium. The collected medium was centrifuged at 2000×g under 4° C. for 10 minutes to pellet any cellular debris. The supernatant containing the viral vector was taken and filtered through a 0.45 μm filter to further remove cell debris. Then the filtered sample was placed under 4° C. for short-term storage or under −80° C. for long-term storage.

It should now be appreciated from all of the above that one of the additional features of the 3D bioreactor disclosed herein is that one may now design a 3D bioreactor, for expansion of viral vector producing cells, with particular geometric and void volume requirements, and corresponding available surface area requirements, and be able to achieve (i.e., during fabrication or manufacturing) such targets with relatively minimal variation. For example, one may now identify a design requirement for a 3D bioreactor wherein the one or more internal voids are to have a targeted void volume "$V_t$", and the 3D bioreactor itself is to have a targeted overall surface area for cell culturing "$SA_t$". Accordingly, one may now form such 3D bioreactor wherein the one or more internal voids have an actual void volume "$V_a$" that is within +/−10.0% of $V_t$, or more preferably, +/−5.0% of $V_t$. Similarly, the actual surface area for cell culturing $SA_a$ is within +/−10.0% of $SA_L$, or more preferably +/−5.0% of $SA_L$. Moreover, one may also identify for the internal surface within the targeted voids a targeted geometry for fabrication such as a targeted radius of curvature "$Rc_t$" and then in fabrication the actual radius of curvature "$Rc_a$" of the void internal surface can now be achieved that is within +/−5% of $Rc_t$.

This invention therefore describes a scalable 3D bioreactor which can reduce from using hundreds of T-flasks to only 3 individual 3D bioreactors of different size for the expansion from $10^5$ to $10^9$ cells. As illustrated in FIG. 15, in order to expand $10^5$ cells to $10^9$ cells, one must utilize 124 T-flasks. By contrast, using three of the 3D bioreactors herein of increasing size, one can more readily achieved this level of cell expansion. In addition, the 3D bioreactor facilitates automatic close-loop cell expansion, which will significantly increase the efficiency in cell expansion and meet the cGMP (current Good Manufacturing Practice) regulatory requirements to expand cells for clinical applications. Furthermore, the use of the 3D bioreactor herein will significantly reduce the use of cell culture mediums. The 3D bioreactor herein is one that scalable with a defined geometry, surface coating, and fluidic dynamics to maintain a monolayer cell culture and reduce or prevent cell aggregation (cell-cell contacting and/or stacking), phenotype change, or extracellular production, and is particularly suitable for the expansion of stem cells, primary cells, and other adherent cells, or non-adherent cells under appropriate surface coating of the bioreactor.

What is claimed:

1. A method for closed-loop expansion of viral vector producing cells and viral vector production comprising:

supplying a three-dimensional bioreactor having an inlet and outlet for the flow of perfusion medium and comprising a plurality of voids having a surface and a surface area for cell expansion, said plurality of voids having a diameter (D), a plurality of pore openings between said voids having a diameter (d), such that D>d and wherein: (a) 90% or more of said voids have a selected void volume (V) that does not vary by more than +/−10.0%; and (b) 90% or more of said pore openings between said voids have a value of d that does not vary by more than +/−10.0%;

said surface of said three-dimensional bioreactor is exposed to UV/ozone treatment, plasma gas treatment or coating with extracellular matrix proteins;

supplying a reservoir for a perfusion medium including oxygen and carbon dioxide;

supplying a perfusion pump in fluid communication with said inlet and outlet of said three-dimensional bioreactor and said reservoir for said perfusion medium;

seeding said three-dimensional bioreactor with adherent viral vector producing cells that attach to the three-dimensional bioreactor surface;

pumping and continuously circulating said perfusion medium from said reservoir into said inlet of said three-dimensional bioreactor and out of said outlet of said three-dimensional bioreactor and promoting viral vector cell expansion;

introducing a transfection medium to said circulating perfusion medium and transfecting said viral vector cells on said three-dimensional bioreactor surface and producing viral vectors; and collecting said viral vectors after transfection.

2. The method of claim 1 wherein said viral vector producing cells comprises HEK 293T cells and said viral vector comprises a lentiviral vector.

3. The method of claim 1 wherein said diameter (D) of said voids is 0.4 mm to 100.0.

4. The method of claim 1 wherein said diameter (D) of said voids is in the range of 0.4 mm to 50.0 mm.

5. The method of claim 1 wherein said diameter (d) of said pore openings is in the range of 0.2 mm to 10.0 mm.

6. The method of claim 1 wherein 95.0% or more of said voids indicate a void volume (V) that does not vary by more than +/−10.0%.

7. The method of claim 1 wherein 99.0% to 100% of said voids indicate a void volume (V) that does not vary by more than +/−10.0%.

8. The method of claim 1 wherein 95.0% or more of said pore openings between said voids have a value of d that does not vary by more than +/−10.0%.

9. The method of claim 1 wherein 99.0 to 100% or more of said pore openings between said voids have a value of d that does not vary by more than +/−10.0%.

10. The method of claim 1 wherein at least 90.0% of the voids present have 2 pore openings per void.

11. The method of claim 1 wherein at least 90.0% of the voids present have 8 to 12 pore openings per void.

12. The method of claim 1 wherein said voids have an internal concave surface.

13. The method of claim 1 wherein said voids comprise spherical voids.

14. The method of claim 13 wherein said spherical voids have a packing efficiency of greater than 64.0% in a 3D cylindrical space.

15. The method of claim 1 wherein said three-dimensional bioreactor is formed from a material that has a Tensile Modulus of at least 0.01 GPa.

16. The method of claim 1 wherein said three-dimensional bioreactor is formed from a material that is biocompatible.

17. The method of claim 1 wherein said three-dimensional bioreactor is formed from a material not susceptible to hydrolysis during cell expansion such that the amount of hydrolysis does not exceed 5.0% by weight of the material present.

18. The method of claim 1 wherein said three-dimensional bioreactor has a diameter ϕ and a height H and the ratio ϕ:H has a value in the range of greater than 1:1 to 100:1.

* * * * *